US011285486B2

(12) United States Patent
Buse

(10) Patent No.: US 11,285,486 B2
(45) Date of Patent: Mar. 29, 2022

(54) COVER ASSEMBLY AND RELATED METHODS OF USE

(71) Applicant: Gen-Probe Incorporated, San Diego, CA (US)

(72) Inventor: David A. Buse, San Diego, CA (US)

(73) Assignee: GEN-PROBE INCORPORATED, San Diego, CA (US)

(*) Notice: Subject to any disclaimer, the term of this patent is extended or adjusted under 35 U.S.C. 154(b) by 252 days.

(21) Appl. No.: 15/934,758

(22) Filed: Mar. 23, 2018

(65) Prior Publication Data

US 2018/0272343 A1    Sep. 27, 2018

Related U.S. Application Data

(60) Provisional application No. 62/476,246, filed on Mar. 24, 2017.

(51) Int. Cl.
*B01L 3/00* (2006.01)
*C12Q 1/6806* (2018.01)
(Continued)

(52) U.S. Cl.
CPC ......... *B01L 3/50853* (2013.01); *B01L 3/5027* (2013.01); *B01L 3/50857* (2013.01);
(Continued)

(58) Field of Classification Search
CPC .............. B01L 3/50853; B01L 3/5027; B01L 3/50857; B01L 9/06; B01L 9/00;
(Continued)

(56) References Cited

U.S. PATENT DOCUMENTS 5,033,820 A * 7/1991 Hama .................. G02B 26/007
                                                       359/889
5,290,521 A * 3/1994 DeStefano, Jr. .......... B01L 3/02
                                                       422/563
(Continued)

FOREIGN PATENT DOCUMENTS

EP       0903176 A2    3/1999
WO    9954031 A1    10/1999
(Continued)

OTHER PUBLICATIONS

PCT, International Search Report and Written Opinion, International Application No. PCT/US2018/024175, dated Jun. 21, 2018.
(Continued)

*Primary Examiner* — Benjamin R Whatley
*Assistant Examiner* — Curtis A Thompson
(74) *Attorney, Agent, or Firm* — Bookoff McAndrews, PLLC; Charles B. Cappellari

(57) ABSTRACT

A cover assembly may include a tray assembly frame, a first cover supported by the tray assembly frame, the first cover extending in a first plane and defining one or more first openings; a second cover supported by the tray assembly frame, the second cover extending in a second plane and defining one or more second openings, wherein the first and second planes are different planes, and wherein the second cover is disposed above the first cover. The cover assembly may include one or more tray holders, each tray holder being configured to hold at least one tray in an upright orientation, wherein each tray holder is moveable between an open position and a closed position, the tray holders being accessible for loading or removing the trays in the open position, and the tray holders being positioned beneath the first and second covers in the closed position.

39 Claims, 18 Drawing Sheets

(51) Int. Cl.
  *B01L 9/06* (2006.01)
  *C12Q 1/686* (2018.01)
  *B01L 3/02* (2006.01)
  *C12Q 1/68* (2018.01)
  *B01L 9/00* (2006.01)

(52) U.S. Cl.
  CPC ............... *B01L 9/06* (2013.01); *C12Q 1/686* (2013.01); *C12Q 1/6806* (2013.01); *B01L 3/0227* (2013.01); *B01L 3/0237* (2013.01); *B01L 9/00* (2013.01); *B01L 2200/021* (2013.01); *B01L 2300/045* (2013.01); *C12Q 1/68* (2013.01)

(58) Field of Classification Search
  CPC ............ B01L 2200/021; B01L 3/0227; B01L 2300/045; B01L 3/0237; C12Q 1/686; C12Q 1/6806; C12Q 1/68
  See application file for complete search history.

(56) References Cited

U.S. PATENT DOCUMENTS

| | | | |
|---|---|---|---|
| 7,597,854 B1 * | 10/2009 | Reynolds | B01L 9/54 422/511 |
| 7,713,487 B1 * | 5/2010 | Locklear | B01L 3/5085 422/501 |
| 2007/0009396 A1 * | 1/2007 | Ho | B01L 3/50853 422/400 |
| 2011/0143947 A1 * | 6/2011 | Chamberlin | G01N 33/56983 506/7 |
| 2014/0038192 A1 * | 2/2014 | Buse | G01N 21/6452 435/6.12 |

FOREIGN PATENT DOCUMENTS

| | | |
|---|---|---|
| WO | 9957561 A2 | 11/1999 |
| WO | 2007005719 A2 | 1/2007 |
| WO | 2011/017094 A2 | 2/2011 |
| WO | 2014/022532 A2 | 2/2014 |

OTHER PUBLICATIONS

PCT International Preliminary Report on Patentability, International Application No. PCT/US2018/024175, dated Sep. 24, 2019.
CNIPA First Office Action, Chinese Patent Application No. 201880019723.2, dated Mar. 26, 2021.
CNIPA Search Report, Chinese Patent Application No. 201880019723.2, dated Mar. 12, 2021.

* cited by examiner

COVER ASSEMBLY AND RELATED METHODS OF USE

CROSS-REFERENCE TO RELATED APPLICATION(S)

This patent application claims the benefit under 35 U.S.C. § 119 to U.S. Provisional Patent Application No. 62/476,246, filed on Mar. 24, 2017, the entirety of which is incorporated herein by reference.

TECHNICAL FIELD

This disclosure is directed to a cover assembly, and related methods of use.

BACKGROUND

Automated analytical procedures for determining the presence of an analyte in a sample typically require the use, processing, and/or manipulation of fluid solutions and/or fluid suspensions. Such fluid solutions and/or suspensions are frequently stored within analytical instruments in containers that may be accessed by a fluid transfer apparatus (e.g., a robotic pipettor). The contents of the containers may be accessed through open ends of the containers (e.g., uncapped and exposed to the atmosphere) during the operation of an instrument. Leaving a container in an open state, however, may lead to contamination of samples contained therein by accidental dripping of material from the pipettor into the open containers.

SUMMARY OF THE DISCLOSURE

In one aspect, the disclosure is directed to a cover assembly comprising a tray assembly frame; a first cover supported by the tray assembly frame, the first cover extending in a first plane and defining one or more first openings; a second cover supported by the tray assembly frame, the second cover extending in a second plane and defining one or more second openings, wherein the first and second planes are different planes, and wherein the second cover is disposed above the first cover; one or more tray holders, each tray holder being configured to hold at least one tray in an upright orientation, wherein each tray holder is moveable between an open position and a closed position, the tray holders being accessible for loading or removing the trays in the open position, and the tray holders being positioned beneath the first and second covers in the closed position; one or more actuators coupled to the tray assembly frame and to the first and second covers, the actuators being configured to move the first and second covers between a closed configuration and one or more open configurations, wherein the tray holders are inaccessible from any position directly above the first and second covers in the closed configuration, and wherein at least one of the first openings and at least one of the second openings are aligned to permit access to a portion of at least one of the tray holders in the open configuration.

The cover assembly includes a cover frame coupled to at least a portion of a top surface of the tray assembly frame and dimensioned to permit access to the tray holders, the cover frame including at least two opposed, upwardly extending guide rails configured to limit longitudinal movement of the first and second covers, wherein each guide rail includes an inwardly extending tab configured to limit vertical movement of the first and second covers. The cover assembly includes one or more guide pins extending upwardly from or through the cover frame, the first cover defining one or more laterally extending, first guide slots that accommodate the guide pins, the second cover defining one or more laterally extending, second guide slots that accommodate the guide pins, wherein each of the first and second guide slots is associated with one of the guide pins, wherein the first and second guide slots are coextensive with each other, and wherein the guide pins and the first and second guide slots are dimensioned to limit lateral movement of the first and second covers. The cover frame is configured to limit vertical movement of one or more trays held by the one or more tray holders. The first and second planes are substantially parallel to each other. The first and second covers are configured for sliding engagement. The first cover defines a plurality of first openings. The second cover defines a plurality of second openings. In each of the open configurations, each of the first openings is aligned with a corresponding one of the second openings, and wherein each of the aligned first and second openings permits access to a portion of at least one of the tray holders in the open configurations. For each of the first openings there is a corresponding one of the second openings. The first and second covers have substantially the same dimensions, and wherein the locations and dimensions of the holes defined by the first and second covers are substantially the same. The first cover and the second cover are arranged as mirror images of each other. The first plane is defined by a first longitudinal axis and a first lateral axis that is perpendicular to the first longitudinal axis, the first cover being configured to move in the first plane along the first lateral axis and not along the first longitudinal axis, and wherein the second plane is defined by a second longitudinal axis and a second lateral axis that is perpendicular to the second longitudinal axis, the second cover being configured to move in the second plane along the second lateral axis and not along the second longitudinal axis. The actuators are configured to move the first and second covers independent of each other. The actuators comprise first and second actuators, the first actuator including a first motor coupled to the first cover and the second actuator including a second motor coupled to the second cover. The first cover comprises a first edge that defines a first end tab and a first lateral edge opposite the first edge, and wherein the second cover comprises a second edge that defines a second end tab and a second lateral edge opposite the second edge. The first end tab defines a first slot, the first actuator includes a first pin, the first slot receives the first pin, and rotation of the first pin causes linear movement of the first cover, and wherein the second end tab defines a second slot, the second actuator includes a second pin, the second slot receives the second pin, and rotation of the second pin causes linear movement of the second cover. In the closed configuration, each first opening of the first cover is blocked by the second cover and each second opening of the second cover is blocked by the first cover. The first and second openings are linear openings. The width of each linear opening is from about 5 mm to about 15 mm. The width of each linear opening is at least about 10 mm. The length of each linear opening is from about 5 to about 15 times the width of the linear opening. The length of each linear opening is about 10 times the width of the linear opening. The cover assembly includes one or more drawers, each tray holder being coupled to one of the drawers, and each drawer being coupled to a drawer face for moving the tray holders between the open and closed positions.

In another aspect, the disclosure is directed to a system comprising a cover assembly; and a fluid transfer device capable of movement over the cover assembly.

The fluid transfer device is capable of movement along the XYZ axes. The fluid transfer device comprises a pipettor having a fixed or disposable tip, and wherein the tray holders hold at least one tray supporting or comprising a plurality of receptacles. The tray is a microtiter plate, and wherein each of the plurality of receptacles of the microtiter plate is a well for containing a fluid. The receptacles are arranged in rows, each row comprising two or more receptacles, and wherein a content of each receptacle of at least one row of receptacles is accessible by the fluid transfer device when the first and second covers are in a first one of the open configurations, and wherein a content of each receptacle of least one row of receptacles is inaccessible by the fluid transfer device when the first and second covers are in the first one of the open configurations. The distance between the centers of the first and second rows is about 10 mm. The first openings comprise a pair of adjacent first openings, the distance between the centers of the adjacent first openings being about 30 mm, and wherein the second openings comprise a pair of adjacent second openings, the distance between the centers of the adjacent second openings being about 30 mm. The tray holders hold at least one tray comprising one or more rows of wells, the wells of each row supporting at least one receptacle and at least one cap positioned in a side-by-side relationship, the cap being configured to close the receptacle, wherein the fluid transfer device is configured for engaging the cap in a frictional fit, and wherein contents of each well of at least one row of wells is accessible by the fluid transfer device when the first and second covers are in at least one of the open configurations. In the closed configuration, the first and second covers are arranged to block the fluid transfer device from aspirating a fluid from or dispensing a fluid into any of receptacles. The system further comprises at least one of: one or more first sensors coupled to the fluid transfer device, the one or more first sensors being configured to track a location of the fluid transfer device; and one or more second sensors coupled to the cover assembly, the one or more second sensors being configured to track locations of the first and second covers.

In yet another aspect, the disclosure is directed to a method of aspirating or dispensing fluid with a system having a first cover, a second cover, and a fluid transfer device, wherein the first cover and the second cover are disposed above a plurality of receptacles, the method comprising the steps of (a) transitioning the first cover and the second cover from a first closed configuration, where access to at least a first group of the plurality of receptacles by the fluid transfer device is blocked by at least one of the first cover and the second cover, to a first open configuration where a first receptacle of the first group of receptacles is accessible by the fluid transfer device; (b) aspirating a fluid from the first receptacle using the fluid transfer device or dispensing a fluid into the first receptacle using the fluid transfer device; (c) after step (b), transitioning the first cover and the second cover from the first open configuration to the first closed configuration, or to a second closed configuration where access to at least a second group of the plurality of receptacles by the fluid transfer device positioned above the first cover and the second cover is blocked by at least one of the first cover and the second cover.

The first cover and the second cover move independent of each other during the transitioning steps. The inserting step includes lowering the fluid transfer device through a first opening of the first cover and a second opening of the second cover. The first cover is disposed in a first plane, the second cover is disposed in a second plane parallel to the first plane, and the first opening is aligned with the second opening in the first open configuration, thereby permitting the fluid transfer device to access the first receptacle. In step (c), the first cover and the second cover are transitioned to the second closed configuration, and in the second closed configuration, a subset of the receptacles are accessible by the fluid transfer device. Prior to step (a) or after step (c), the step of moving the fluid transfer device along a path that extends over at least one receptacle of the plurality of receptacles, the path being covered by at least one of the first and second covers. After step (c) and prior to aspirating a fluid from a second receptacle using the fluid transfer device or dispensing a fluid into the second receptacle using the fluid transfer device, the step of transitioning the first and second covers to a second open configuration where the second receptacle is accessible by the fluid transfer device and access to the first receptacle by the fluid transfer device is blocked by at least one of the first cover and the second cover. The method further comprises the step of aspirating a fluid from the second receptacle using the fluid transfer device or dispensing a fluid into the second receptacle using the fluid transfer device. One of the first and second covers is stationary when transitioning the first cover and the second cover from the first closed configuration to the first open configuration. The first and second covers move simultaneously when transitioning the first and second covers from the first closed configuration to the first open configuration. The first and second covers move sequentially when transitioning the first and second covers from the first closed configuration to the first open configuration. The method further comprises prior to step (a), the step of providing one or more trays to the system below the first and second covers, each tray supporting or comprising at least a portion of the plurality of receptacles. Each tray comprises a plurality of wells, each well being configured to hold one of the receptacles or a cap for closing the receptacle, and each receptacle being a vial. The method further comprising, with the fluid transfer device, the steps of engaging a cap supported by a first well of the plurality wells in a frictional fit and sealing a vial in a second well of the plurality of the wells with the cap, thereby forming a cap/vial assembly, wherein the first and second wells are adjacent wells. The method further comprising, while the cap of the cap/vial assembly is engaged by the fluid transfer device, moving the cap/vial assembly from a first location of the system where the engaging step is performed to a second location of the system. The second location of the system is a centrifuge or a thermal cycler. Step (b) comprises dispensing the fluid into the first receptacle, and wherein the fluid is a reaction fluid for performing a PCR reaction. After step (a) and prior to step (c), a row of the receptacles is accessible by the fluid transfer device, the row of receptacles including the first receptacle. The method further comprising, prior to step (b), the step of inserting a fixed or disposable tip of the fluid transfer device into the first receptacle.

BRIEF DESCRIPTION OF THE FIGURES

The accompanying drawings, which are incorporated in and constitute a part of this specification, illustrate various examples and together with the description, serve to explain the principles of the disclosure.

DETAILED DESCRIPTION

Reference will now be made in detail to examples of the present disclosure, which are illustrated in the accompanying drawings. Wherever possible, the same reference numbers will be used throughout the drawings to refer to the same or like parts. In the discussion that follows, relative terms such as "about," "substantially," "approximately," etc. are used to indicate a possible variation of ±10% in a stated numeric value.

Diagnostic System

Figure 1:
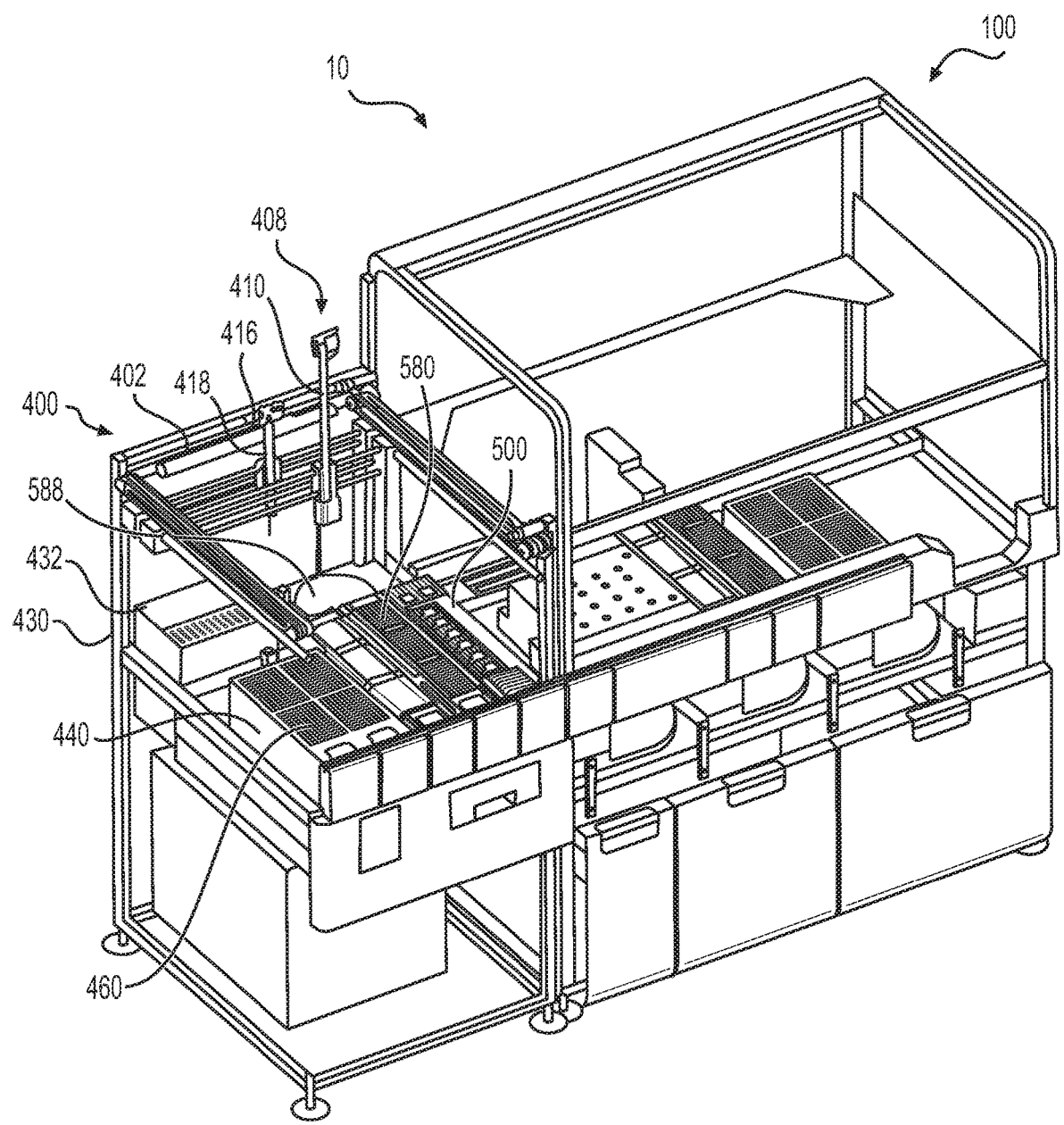
FIG. 1 is a perspective view of a diagnostic system comprising a first module and a second module.

FIG. 1 illustrates a diagnostic system 10 configured to perform a plurality of different molecular assays on a plurality of samples. In some examples, diagnostic system 10 may be configured to perform different target nucleic acid amplification reactions. For example, diagnostic system 10 may be configured to perform a first target nucleic acid amplification reaction on a first subset of a plurality of samples, and perform a second, different target nucleic acid amplification reaction on a second subset of the plurality of samples. System 10 may perform any number of different reactions on different samples. In some examples, diagnostic system 10 comprises a first module 100 configured to perform at least one of the steps of a target nucleic acid amplification reaction, and a second module 400 configured to perform at least one of the steps of the target nucleic acid amplification. Diagnostic system 10 may include any of the components and functionalities described in U.S. Patent Application Publication Nos. 2016/0032358, 2014/0038192, and 2014/0263984.

Diagnostic system 10 may be configured such that first module 100 may be selectively and operatively coupled to second module 400, and first module 100 may be selectively decoupled from second module 400. This coupling may be achieved by any suitable mechanism(s), such as, e.g., mechanical fasteners (for example, bolts screws, or clamps). Suitable power and/or data lines may be provided between second module 400 and first module 100. In some examples, second module 400 may extend the overall system capabilities of a diagnostic system including only first module 100 that was previously purchased by a customer or otherwise used by an operator.

First Module

First module 100 may include various components configured to receive one or more reaction receptacles, within each of which is performed one or more steps of a multi-step nucleic acid test (NAT) designed to detect, for example, a virus or organism (e.g., bacterium, fungus, or protozoan). As the focus of this disclosure includes components within second module 400, this disclosure refers to U.S. Patent Application Publication No. 2016/0032358 for additional details of exemplary first modules 100.

Second Module

Second module 400 may be integral with first module 100, and in other examples, second module 400 may be selectively and operatively coupled to first module 100 as described above.

In one example, second module 400 is configured to perform nucleic acid amplification reactions, for example, PCR, and, in certain examples, to measure fluorescence in real-time (e.g., as the amplification reaction is occurring). A controller may direct the components of first module 100, and components of second module 400, to perform the assay steps. In one example, first module 100 houses a computer and all fluids, reagents, consumables, and mechanical modules needed to perform the specified amplification-based assays, such as assays based on transcription-based amplification methods, for example, TMA or nucleic acid sequence-based amplification (NASBA). TMA methods are described in U.S. Pat. Nos. 5,399,491 and 5,480,784; and NASBA methods are described in U.S. Pat. No. 5,409,818 and in U.S. Pat. No. 5,130,238. As explained above, the controller may comprise a computer and preferably can accommodate LIS ("laboratory information system") connectivity and remote user access. In some examples, second module 400 houses component modules that enable additional amplification assays, melting analyses, and additional functionalities. Other components may include a printer and an uninterruptible power supply.

Figure 2:
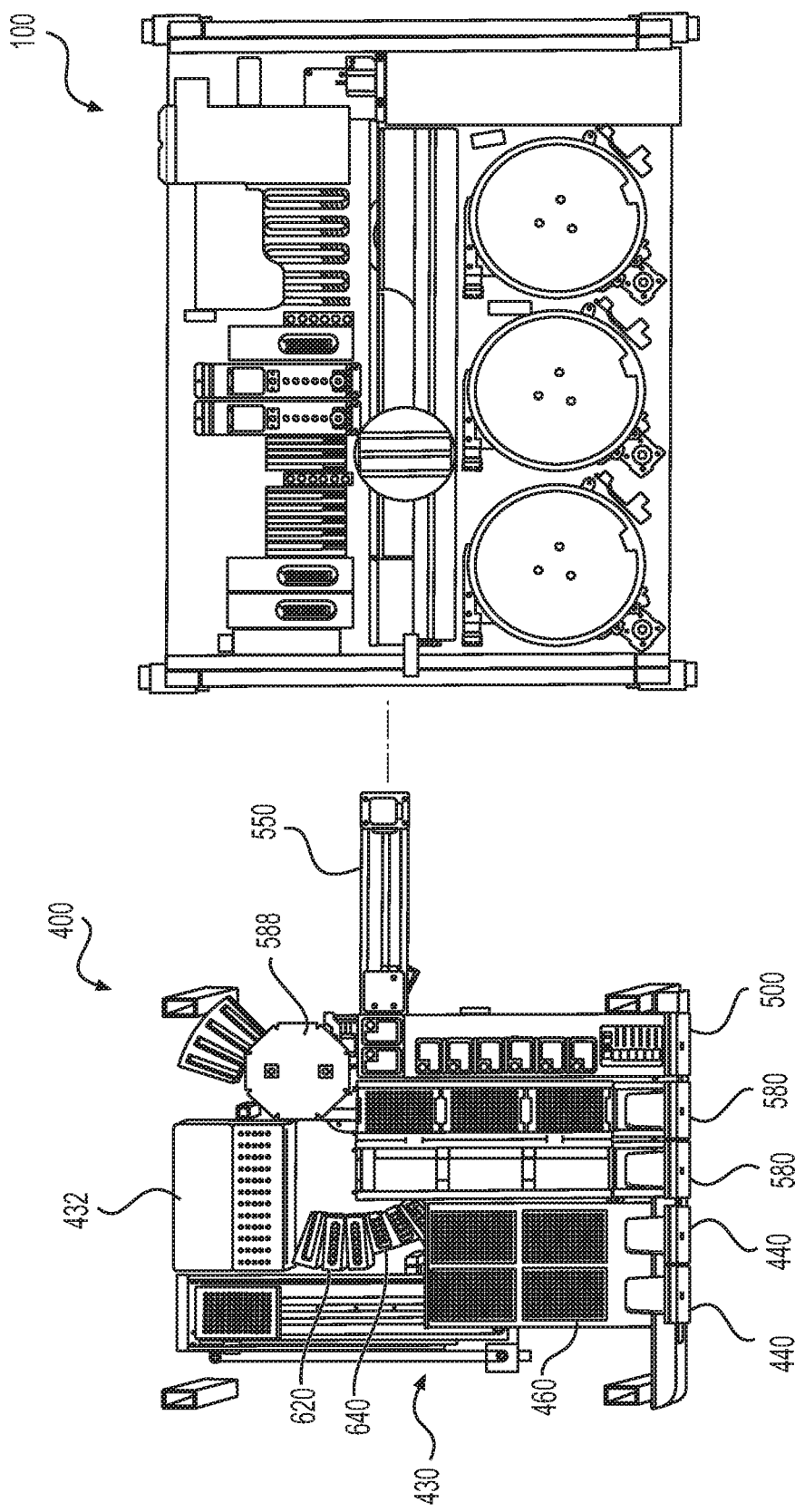
FIG. 2 is an exploded, top plan view of the first module and the second module of FIG. 1.
Figure 3:
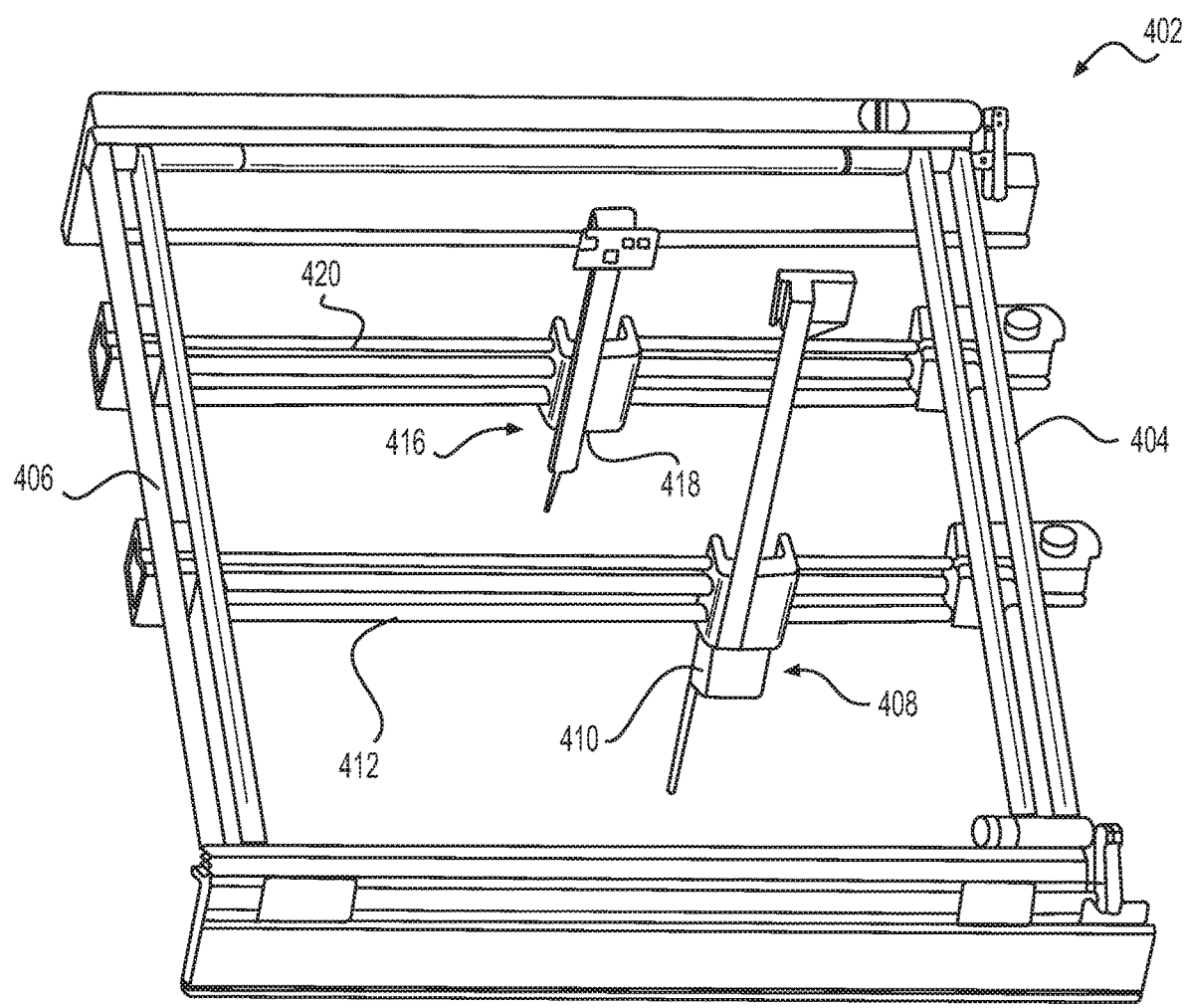
FIG. 3 is a perspective view of a robotic pipettor of the second module of FIG. 1.

Examples of the general configuration of second module 400 are shown in FIGS. 1-3. Second module 400 can include, for example, a substance transfer device (for example, a fluid transfer device or robotic pipettor 402), a thermal cycler/signal detector 432, tip compartments 580 (e.g., two or more) configured to contain trays of disposable tips for the pipettor(s), tray assemblies 440 (e.g., two or more) configured to contain trays 460 of disposable processing vials and associated caps in an upright orientation, a bulk reagent container compartment 500, and a bulk reagent container transport 550. For purposes of this disclosure, a fluid transfer device may be referred to in the exemplary embodiments described herein, which is not intended to limit this disclosure from encompassing the use of other suitable substance transfer devices.

Figure 19:
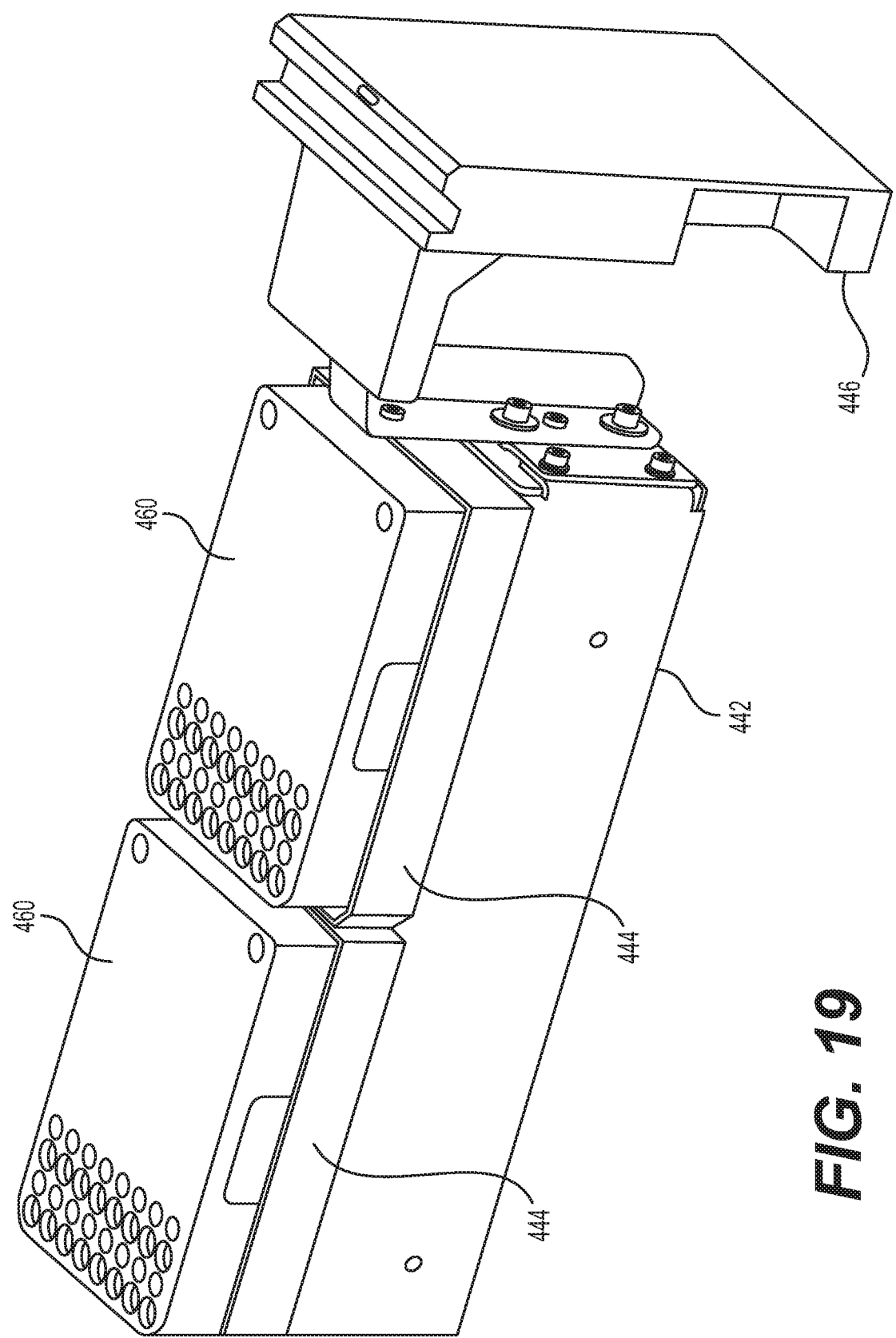
FIG. 19 is a perspective view of a drawer of the tray assembly of FIG. 16.

As shown in FIG. 1, components of second module 400 may be positioned on different levels, or decks, arranged vertically within a chassis of second module 400. Fluid transfer device 402 is disposed near the top of second module 400, above all other components, in some examples. The vertical order of the decks and components may vary according to the intended use of diagnostic system 10. In the depicted example, below fluid transfer device 402, an amplification processing deck 430 includes the bulk reagent container compartment 500 and bulk reagent container transport 550, a centrifuge 588, the top of the thermal cycler/signal detector 432, tip compartments 580, and tray assembly 440. Tray assembly 440 may include a tray assembly frame 450 (referring to FIG. 16) mountable to the chassis of second module 400, and may include drawers 442 (referring to FIG. 19) movable between an open position and a closed position via drawer faces (handles) 446. Drawers 442 may include one or more tray holders 444 (e.g., exactly two), each configured to receive a tray 460 (shown in, e.g., FIGS. 17 and 19, where each tray is shown with only some of its respective wells/receptacles). An exemplary tray is described in U.S. Patent Application Publication No. 20170297027A1. Tray holders 444 may be accessible for loading or removing trays 460 in the open position, and are positioned beneath covers of a cover assembly in the closed position (e.g., first and second covers 2002 and 2004 of a cover assembly 2000, described below). Below the amplification processing deck 430, magnetic elution slots 620 and reagent pack loading stations 640 on a receptacle processing deck are accessible to fluid transfer device 402 through a gap between modules of the amplification processing deck 430.

Fluid Transfer Device

Figure 4:
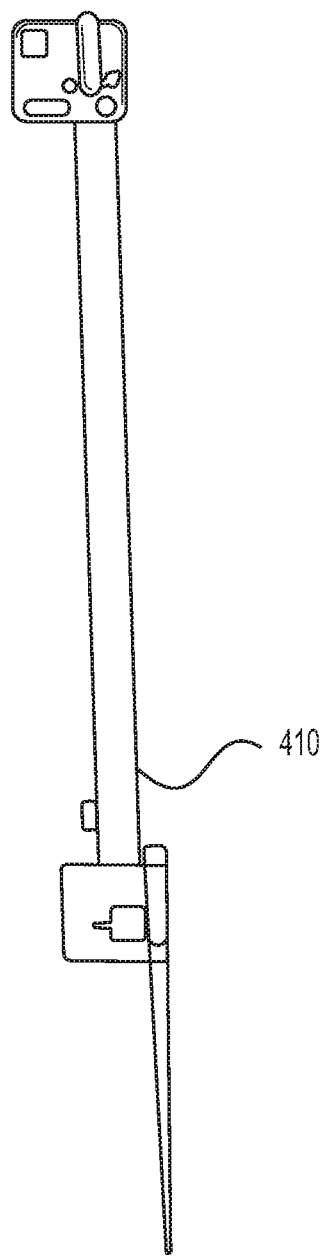
FIG. 4 is a perspective view of a substance transfer pipettor of the robotic pipettor of FIG. 3.

Fluid transfer device 402, shown in FIGS. 1, 3, and 4, may be a dual arm system comprising a front arm 408 and a back arm 416. Fluid transfer device 402 may be configured to dispense and/or aspirate substances into and/or from a container, receptacle, well, etc., in second module 400. Front arm 408 includes a substance transfer pipettor 410 configured to aspirate fluid and dispense fluid, and includes a pump, for example, an integrated syringe pump. Back arm 416 includes a vial transfer arm 418 and may not perform substance transfer. Fluid transfer device 402 comprises a Cartesian gantry assembly with two transverse tracks 404, 406, a back arm longitudinal track 420, and a front arm longitudinal track 412. The designations "longitudinal" and "transverse" are merely for distinguishing the two sets of tracks, which may be orthogonal to one another, but otherwise the designations are arbitrary.

Substance transfer pipettor 410 may be driven back and forth along front arm longitudinal track 412 by a belt, drive screw, or other motion transmission device coupled to a motor. Vial transfer arm 418 may be driven back and forth along back arm longitudinal track 420, front arm longitudinal track 412 may be driven back and forth along transverse tracks 404, 406, and back arm longitudinal track 420 may be driven back and forth along transverse tracks 404, 406, by similar mechanisms. Substance transfer pipettor 410 and vial transfer arm 418 may be movable simultaneously along multiple axes, such as, e.g., the X and Y axes. For example, substance transfer pipettor 410 may be moved along front arm longitudinal track 412 at the same time that front arm longitudinal track 412 is moved along transverse tracks 404 and 406. Similarly, vial transfer arm 418 may be moved simultaneously along the same axes by moving vial transfer arm 418 along back arm longitudinal track 420 at the same time that back arm longitudinal track 420 is moved along transverse tracks 404 and 406. The movement of substance transfer pipettor 410 and vial transfer arm 418 along multiple axes at the same time may allow for more direct and efficient paths of those devices between desired locations, potentially resulting in reduced procedure times. Substance transfer pipettor 410 and vial transfer arm 418 also may be driven along the Z, or vertical, axis for example, by a motor and/or other suitable device. The Z axis may be substantially perpendicular to both the X and Y axes, and may correspond to the up/down direction within second module 400.

In some examples, the motors of fluid transfer device 402 may be under the control of a system controller. The motors may be stepper motors and may include rotary encoders for controlling and monitoring the position of the track or pipettor to which it is coupled. Each of the tracks has home sensors (or limit switches) for indicating when substance transfer pipettor 410 or vial transfer arm 418 is in one or more designated positions, such as a designated "home" position. Similarly, each device may have a vertical home sensor for indicating when the probe is in one or more designated vertical positions, such as a designated vertical "home" position. Such sensors for indicating a home position may include optical sensors (e.g., slotted optical sensors), proximity sensors, magnetic sensors, capacitive sensors, etc.

In one example, substance transfer pipettor 410 is configured to accept TECAN 1 mL disposable pipette tips by inserting the probe thereof into a disposable pipette tip, and an interference fit between the probe and the pipette tip frictionally secures the pipette tip to the end of the probe. Front arm 408 and substance transfer pipettor 410 are configured to access at least parts of both amplification processing deck 430 and the receptacle processing deck on second module 400. Substance transfer pipettor 410 may include integrated tip sensing for confirming the presence or absence of a disposable pipette tip, capacitive level sensing for detecting contact by the pipette tip with the surface of the fluid contents of a reaction receptacle or other container and determining the level of the fluid contents based on the detected vertical position of the pipettor, and pressure sensing for sensing pressure fluctuations within the substance transfer system during fluid dispensing or aspiration. Vial transfer arm 418 is configured to pick up a cap/vial assembly by inserting the probe thereof into a cap that is coupled to a vial, as will be described below.

Cap/Vial Assembly

Referring to FIGS. 5-8, processing vial 464 provides a receptacle for containing reaction fluids for performing PCR or other processes. Cap 476 is configured to be placed into or onto vial 464 in an automated manner so as to close off vial 464. In some examples, cap 476 is configured to receive an end of vial transfer arm 418 via a friction fit, so that transfer arm 418 can pick up cap 476 and place it into or onto vial 464. Cap 476 and vial 464 are configured to lock together so that once cap 476 is placed into or onto vial 464, cap 464 and vial 476 are interlocked to form a cap/vial assembly. Vial transfer arm 418 can then transfer the cap/vial assembly from one location within second module 400 to another location. Exemplary caps and vials are disclosed in U.S. Provisional Patent Application No. 61/782,320.

Figure 5:
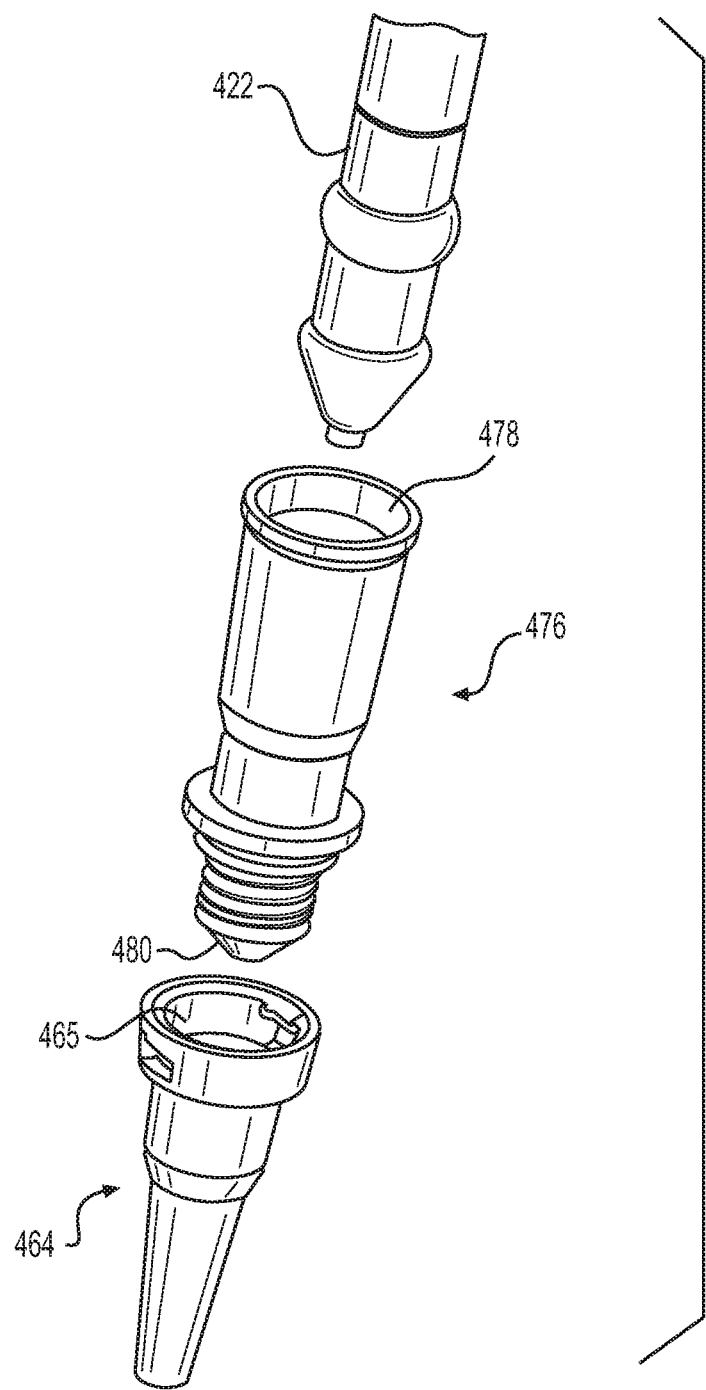
FIG. 5 is an exploded, perspective view of a processing vial, a processing vial cap, and a pipettor probe.
Figure 6:
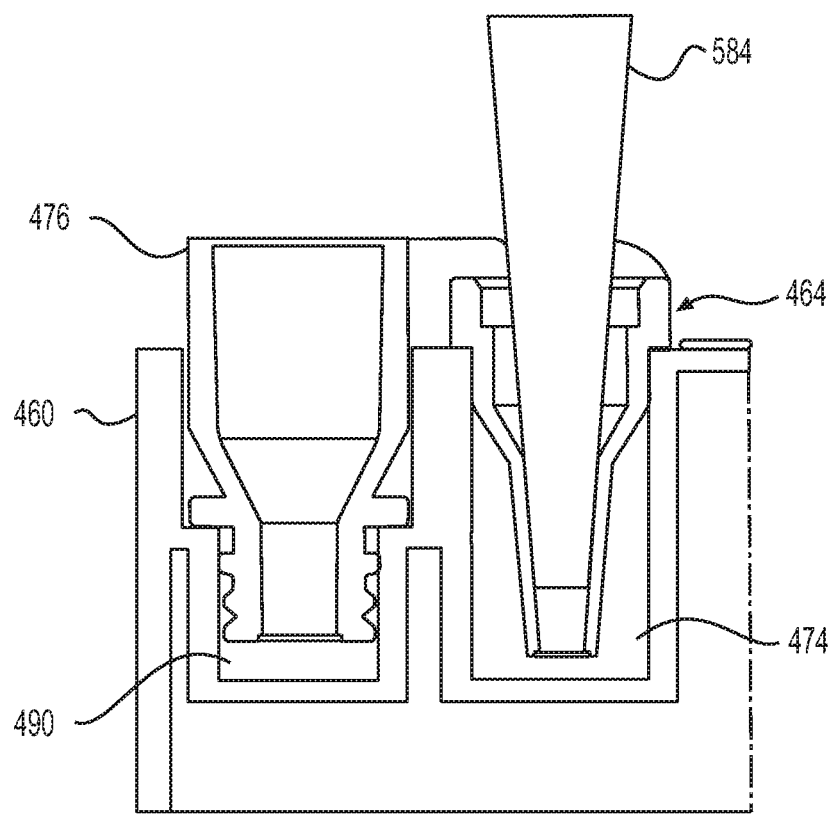
FIG. 6 is a transverse cross-section of the processing vial and the processing vial cap disposed within a processing vial well and a cap well, respectively, of a processing cap/vial compartment tray.
Figure 7:
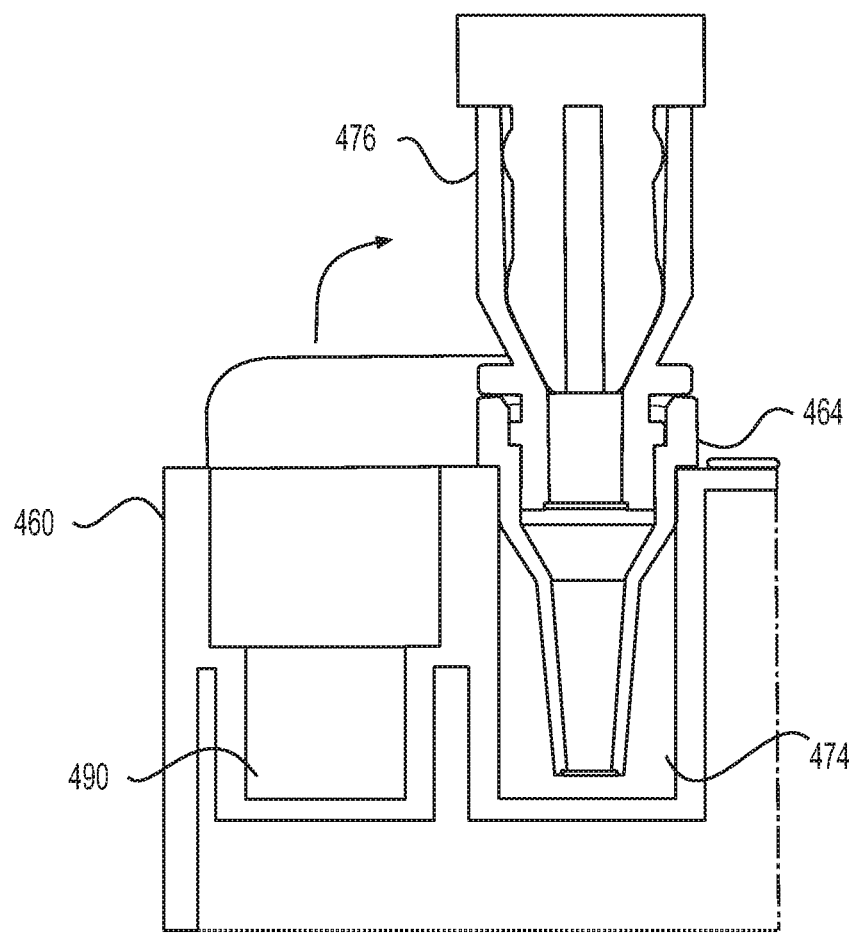
FIG. 7 is a transverse cross-section of the processing vial cap removed from the cap well and inserted into the processing vial with the processing vial disposed within the processing vial well.

In the example shown in FIGS. 5-7, processing vial 464 has a conical shape and an open top end 465. Cap 476 has an open top end 478 and a closed lower end 480. A lower portion of cap 476 defines a plug that fits into open top end 465 of processing vial 464. This plug is sized so as to fit into vial 464 with an interference, friction fit.

The examples illustrated in FIGS. 6 and 7 show, in cross-section, cap 464, initially held in a cap well 490 of tray 460, and vial 464 held in a vial well 474 of tray 460. After fluids are dispensed into vial 464 with a disposable pipette tip 584 (connected to a robotic pipettor), vial 464 is capped by a cap 476 by inserting the closed lower end 480 of cap 476 into open top end 465 of vial 464.

Trays

Figure 8:
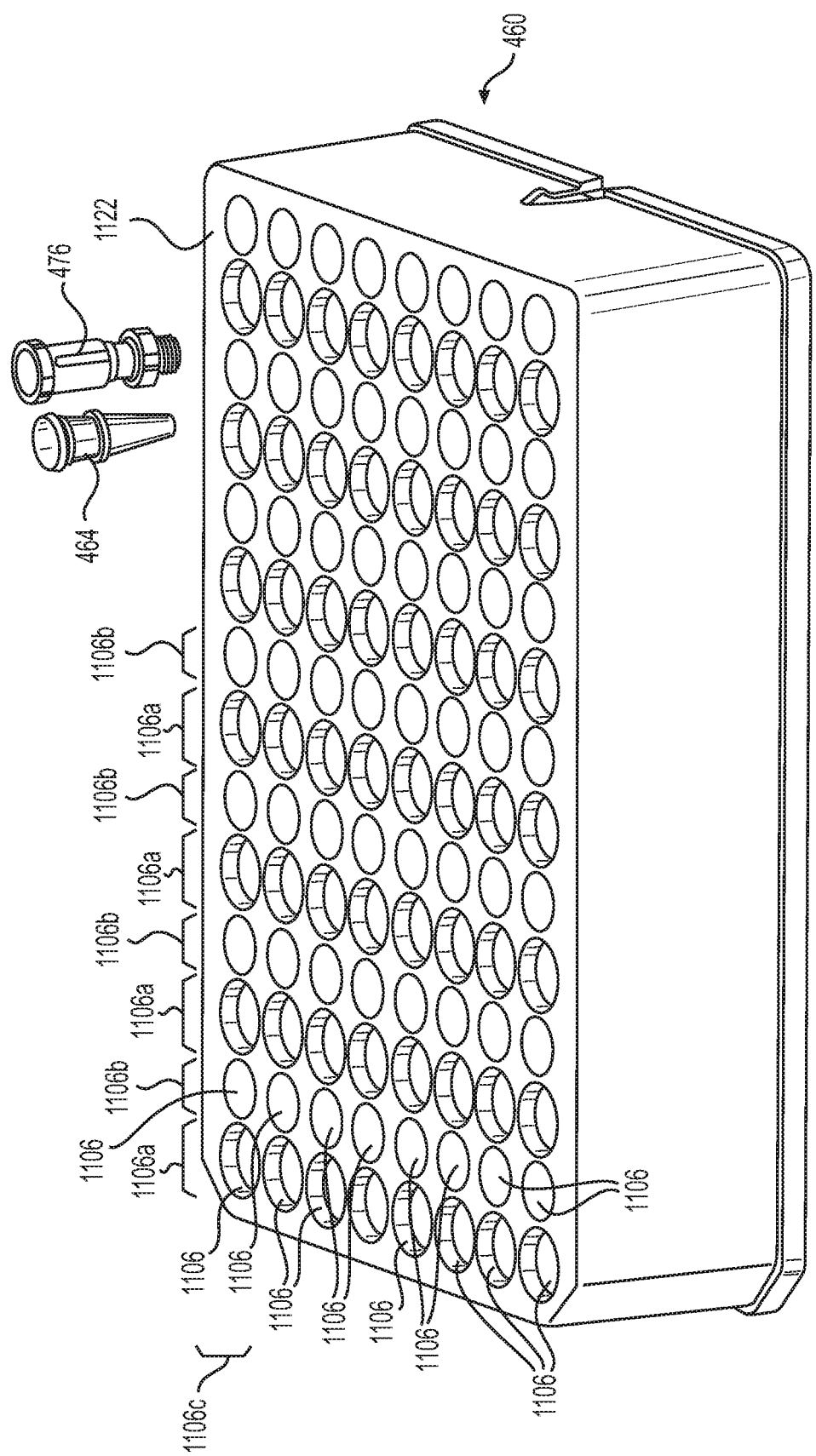
FIG. 8 is a perspective view of a tray with wells for storing the vials and caps shown in FIGS. 5-7.
Figure 9:
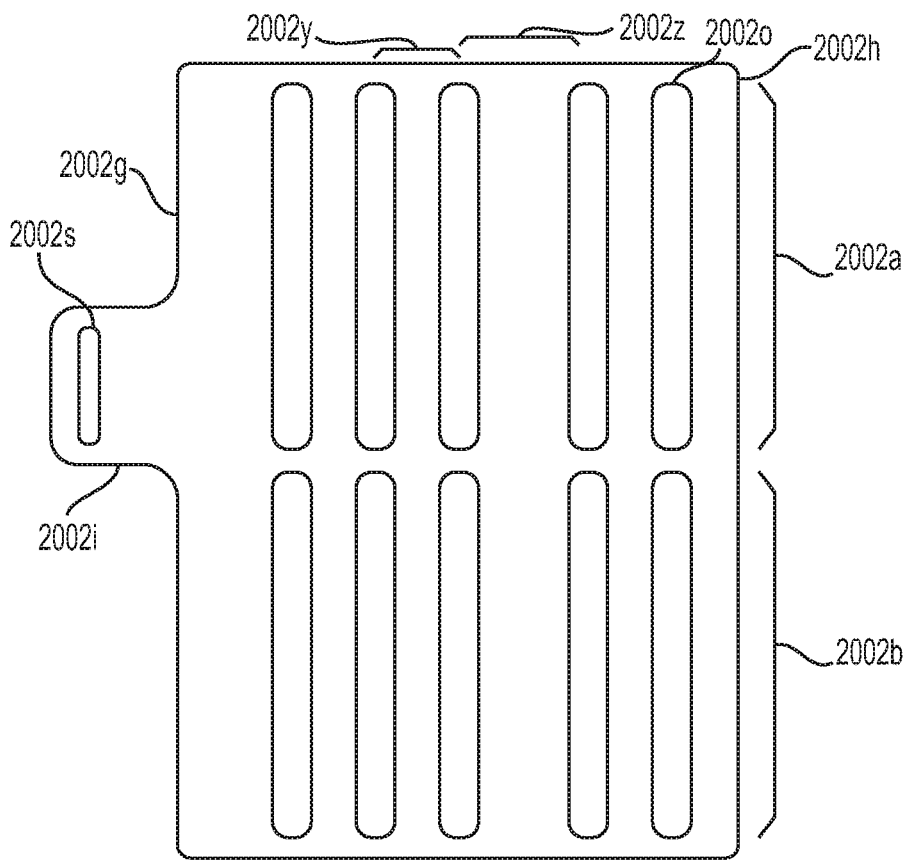
FIGS. 9 and 10 are top views of a first cover and a second cover of a cover assembly.
Figure 10:
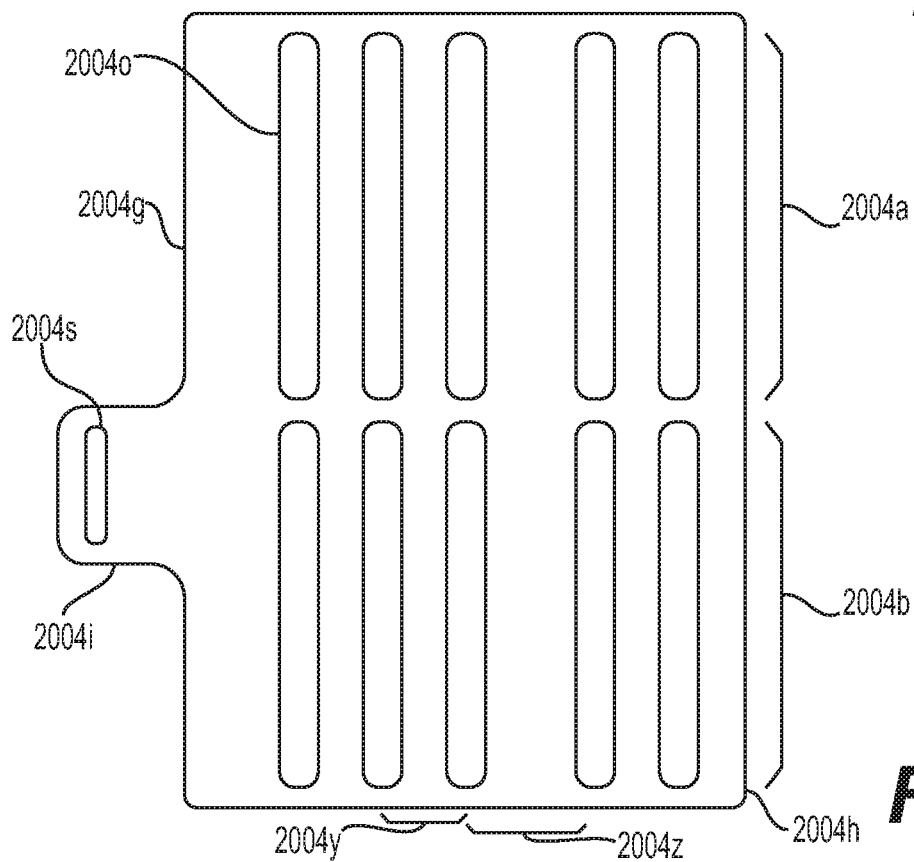

Referring to the illustrative example in FIG. 8, each tray 460 may define a plurality of wells 1106 each configured to receive vials 464 or caps 476. In some examples, each well of the plurality of wells 1106 is configured to receive only one vial 464 or cap 476. Wells 1106 also may be configured to receive other receptacles, containers, pipette tips, or the like. Tray 460 depicted in FIG. 8 is merely illustrative, and is intended to be non-limiting with respect to the embodiments described herein. For example, the embodiments described herein encompass the use of microtiter well plates having a plurality of wells for containing a fluid, self-standing receptacles, other suitable types of holders for retaining receptacle vessels, and the like. Because wells 1106 themselves may contain a fluid (without a separate receptacle), wells 1106, in some embodiments, may be considered receptacles.

In some examples, the plurality of wells 1106 can include two or more subsets of wells 1106, and each subset of wells 1106 may be configured to contain a different item. For example, as shown in FIG. 8, wells 1106 of a first subset 1106*a* are shaped and sized differently than wells 1106 of a second subset 1106*b*.

In some examples as shown in FIG. 1, wells 1106 of first subset 1106*a* can each be configured to contain a (receptacle) vial 464, and wells 1106 of second subset 1106*b* can each be configured to contain a cap 476. Thus, wells 1106 of first subset 1106*a* may be substantially similar to wells 474, and wells 1106, and wells of second subset 1106*b* may be substantially similar to wells 490, described above.

Additionally, as exemplified, wells 1106 of each tray 460 may be arranged in a plurality of columns 1106*c* that extend along a length of tray 460. Each tray may have eight columns 1106*c* and fourteen rows of wells 1106. The fourteen rows may include seven rows of first subset 1106*a* and seven rows of second subset 1106*b*. However, it is contemplated that other suitable numbers of columns and rows may be utilized.

Tray 460 can include a surface 1122 defining the openings of the plurality of wells 1106. Surface 1122 is positioned at the top of tray 460 in some examples as shown in FIG. 8. In some examples, surface 1122 is substantially rectangular when viewed from above. Tray 460 may include any suitable plastic, metal or other material.

Additional details of second module 400 and its components may be found in U.S. Patent Application Publication No. 2016/0032358.

Cover Assembly

Referring to FIGS. 9-14, a cover assembly 2000 may be configured to selectively permit access to the one or more trays 460, and its wells 1106, via front arm 408 and back arm 416 of fluid transfer device 402. In one embodiment, cover assembly 2000 may selectively provide access to various sample wells, vials, microtiter plates, or the like, located on or below amplification deck 430. Cover assembly 2000 may be positioned between fluid transfer device 402 and one or more trays 460 positioned on amplification deck 430. Thus, cover assembly 2000 may be positioned above amplification deck 430 and below fluid transfer device 402. Cover assembly 2000 may include tray assembly frame 450 (referring to FIG. 16), a cover frame 2001 (referring to FIGS. 16 and 17), a first cover 2002, and a second cover 2004. First cover 2002 and second cover 2004 each may be supported by tray assembly frame 450 and cover frame 2001. Cover frame 2001 may be configured to limit the vertical movement of one or more trays 460 held by tray holders 444. First cover 2002 and second cover 2004 may be composed of any suitable material, such as, e.g., injection molded plastic, although other materials, including metals or metal alloys may be used. First cover 2002 and second cover 2004, in some examples, may be composed of absorbent materials on one or more surfaces, including a top surface, to capture any fluid that may leak or drip from fluid transfer device 402. In one embodiment, first cover 2002 and second cover 2004 are made from polyoxymethylene (POM), which may have good sliding properties (e.g., low friction) and high wear resistance.

In various embodiments, cover assembly 2000 may extend along a longitudinal axis 2300, and a lateral axis 2302 that is substantially perpendicular to longitudinal axis 2300. In some examples, cover assembly 2000 may be fixed relative to longitudinal axis 2300 and movable along lateral axis 2302. The dimensions of first cover 2002, second cover 2004, and their respective openings may depend on the size of trays, columns, and wells disposed beneath cover assembly 2000. More particularly, first cover 2002 may extend in a first plane, and second cover 2004 may extend in a second plane that is different and parallel to the first plane. The first plane and the second plane each may include a longitudinal axis that is parallel to longitudinal axis 2300, and a lateral axis that is parallel to lateral axis 2302. First cover 2002 may move along its respective lateral axis, but not along its respective longitudinal axis (i.e., first cover 2002 may be fixed relative to its respective longitudinal axis). Similarly, second cover 2004 may move along its respective lateral axis, but not along its respective longitudinal axis (i.e., second cover 2004 may be fixed relative to its respective longitudinal axis). It should also be noted that the terms "longitudinal" and "lateral" used with respect to cover assembly 2000 do not imply any particular orientation of cover assembly 2000 within a larger system, such as, e.g., second module 400.

In some examples, first cover 2002 and second cover 2004 may be substantially identical to one another. That is, first cover 2002 and second cover 2004 may have substantially the same dimensions, and the locations and dimensions of openings defined by first cover 2002 and second cover 2004 may be substantially the same. In other examples, first cover 2002 and second cover 2004 may have certain differing features. When first cover 2002 and second cover 2004 are substantially identical to one another, when assembled into cover assembly 2000, first cover 2002 and second cover 2004 may be overlaid mirror images of each other. That is, before being assembled into cover assembly 2000, second cover 2004 is rotated 180 degrees about lateral axis 2302 such that second cover 2004 is a mirror image of first cover 2002. Then, second cover 2004 may be overlaid above first cover 2002. First cover 2002 and second cover 2004 each may include a plurality of openings. Each of the openings may be completely defined and surrounded by material of the respective cover in which it is located. In other examples, a portion of one or more of the openings may include a slot or groove disposed in/recessed from an end surface of first cover 2002 or second cover 2004. In various embodiments, it is contemplated that the slot and groove may be sized and shaped differently to accommodate a variety of cap, vial or receptacle holder configurations, e.g., a tray, microtiter well plate, etc. Additionally, each opening in first cover 2002 may have a corresponding opening in second cover 2004 so that a total number of openings in first cover 2002 is equal to a total number of openings in second cover 2004.

Figure 16:
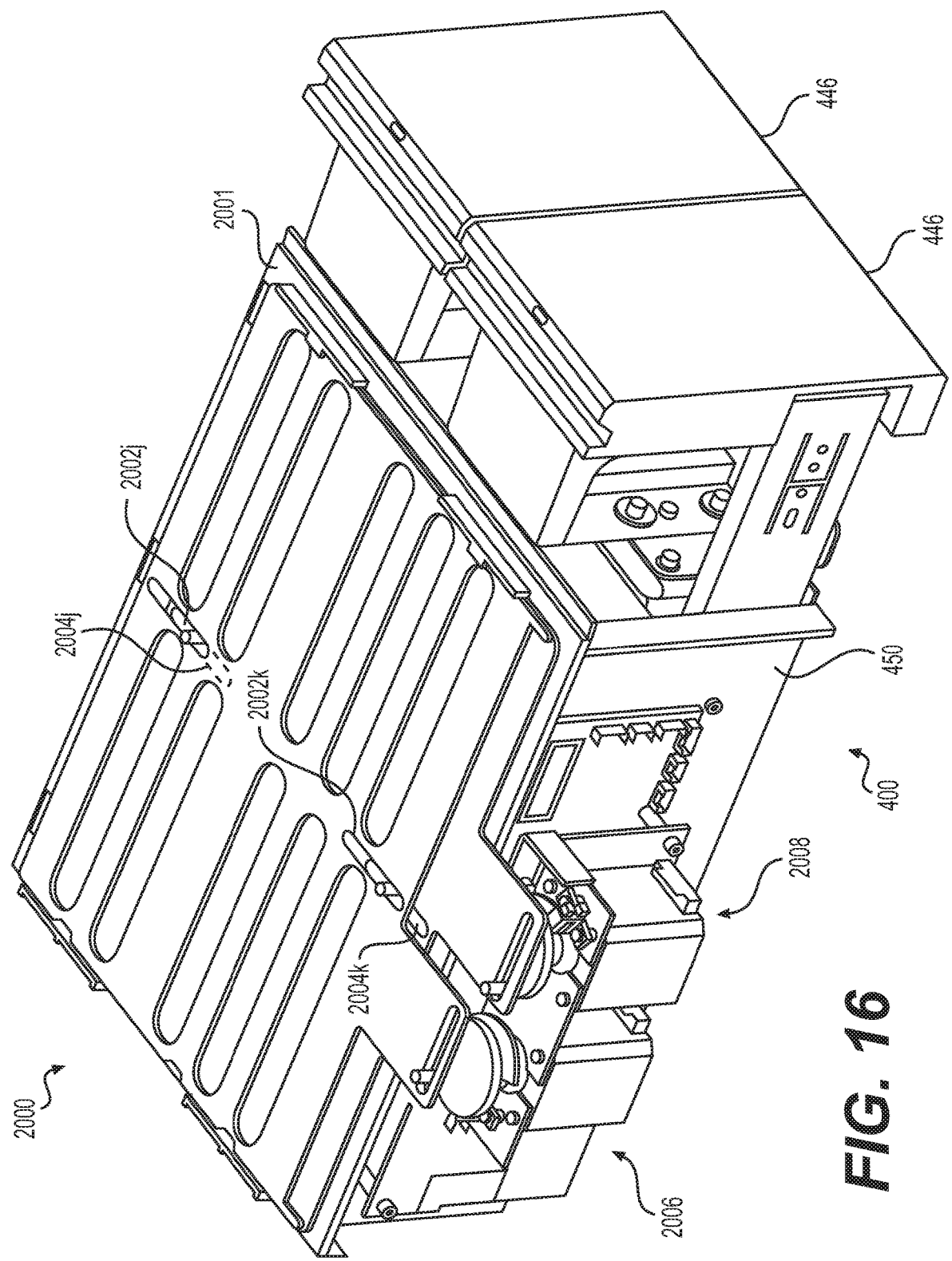
FIG. 16 is a perspective view of a tray assembly and a cover assembly.

First cover 2002 may include a first lateral end surface 2002g, a second lateral end surface 2002h, and an end tab 2002i. End tab 2002i may extend away from first lateral end surface 2002g in a direction opposite of second lateral end surface 2002h, and may include a slot 2002s. Second cover 2004 may include a first lateral end surface 2004g, a second lateral end surface 2004h, an end tab 2004i, and a slot 2004s that are arranged in a substantially similar manner as set forth above with respect to first cover 2002. End tabs 2002i and 2004i may be offset from a centerline along lateral axis 2302 to allow for the connection of end tabs 2002i and 2004i to first motor 2006 and second motor 2008, respectively. In some embodiments, first cover 2002 also may include a first lateral slot 2002j and a first lateral slot 2002k. First lateral slot 2002j may extend lengthwise along the lateral axis of first cover 2002, and may be positioned adjacent to lateral edge 2002h. First lateral slot 2002k may extend lengthwise along the lateral axis of first cover 2002, and may be positioned adjacent to lateral edge 2002g. Second cover 2004 may include a second lateral slot 2004j and a second lateral slot 2004k that are adjacent to lateral edge 2004h and lateral edge 2004g, respectively. In FIG. 16, the dashed lines represent a portion of second lateral slot 2004j hidden from view by top cover 2002. Second lateral slot 2004j and second lateral slot 2004k may be substantially similar, in terms of dimension and orientation relative to adjacent lateral edges, to first lateral slot 2002j and first lateral slot 2002k. First slot 2002j may be coextensive with second slot 2004j, and first slot 2002k may be coextensive with second slot 2004k.

In some examples, first cover 2002 may have a first column 2002a and a second column 2002b of openings 2002o. First column 2002a and second column 2002b are arranged in the direction of lateral axis 2302. Openings 2002o may be any suitable shape including, e.g., rectangular, rounded rectangular, oval, stadium, or the like, Additionally, first cover 2002 may include additional columns of openings 2002o to provide access to additional trays 460 positioned beneath cover assembly 2000. For example, as shown in FIGS. 1 and 2, trays 460 are arranged in a two-by-two grid in second module 400. However, if instead of a two-by-two grid, trays 460 were arranged in a three-by-three grid, first cover 2002 may include three columns of openings 2002o instead of two columns. Each opening 2002o in first column 2002a may be longitudinally spaced (along longitudinal axis 2300) from an opening 2002o in second column 2002b. Laterally adjacent openings 2002o in the same column may be spaced apart (along lateral axis 2302) from one another at various intervals. Some laterally adjacent openings 2002o may be spaced apart from one another at a first interval 2002y, while other laterally adjacent openings 2002o may be spaced apart from one another at a second interval 2002z larger than first interval 2002y (e.g., to account for a gap between laterally adjacent trays 460 beneath cover assembly 2000). Each opening 2002o may be sized to expose a column of wells 1106 from tray 460 positioned underneath cover assembly 2000, thereby allowing access to the column of wells 1106 through the opening 2002o. The size of openings 2002o and the spacing between adjacent openings may be dictated by the size and spacing of wells 1106 beneath cover assembly 2000. Additionally, in some examples, first cover 2002 and/or second cover 2004 may include a single column of openings that provides access to wells in multiple trays.

First cover 2002 may be 296 mm long along longitudinal axis 2300, and 207 mm long along lateral axis 2302 between edges 2002g and 2002h. End tab 2002i may be 53 mm long in the direction of lateral axis 2302 and 50 mm long in the direction of longitudinal axis 2300. Openings 2002o may be about 5 mm to about 15 mm wide, at least about 10 mm wide, about 12.5 mm wide, or another suitable width, and at least about 100 mm long, about 50 mm to about 150 mm long, or at least about 124 mm long. The length of each opening 2002o may be about 5 to about 15 times the width of each opening 2002o, or about 10 times the width of each opening 2002o. In one embodiment, a straight portion of each opening 2002o may be about 124.75 mm long (not including the radiused on each end of the opening) and the overall end-to-end length of an opening 2002o may be about 137.35 mm. The distance between the centers of laterally adjacent openings may be about 31.5 mm. The distance between centers of adjacent rows may be about 10 mm, from about 5 mm to about 15 mm, or about 10.5 mm. These dimensions are merely illustrative, and any other suitable dimensions may also be used.

Second cover 2004 may include a first column 2004a and a second column 2004b of openings 2004o. Openings 2004o may be substantially similar to openings 2002o of first cover 2002. Additionally the arrangement of, number of columns of, and spacings between openings 2004o may be substantially similar in second cover 2004 as the arrangement of, number of columns of, and spacings between openings 2002o in first cover 2002.

First cover 2002 and second cover 2004 may be disposed in parallel planes and may be slidable relative to one another (e.g., configured for sliding engagement so that first cover 2002 and second cover 2004 contact one another), along lateral axis 2302, by one or more actuators. In one example, the one or more actuators may include a first motor 2006, coupled to first cover 2002, and a second motor 2008, coupled to second cover 2004. First motor 2006 and second motor 2008 may be any suitable motor, e.g., a servomotor or stepper motor, configured to independently move first cover 2002 and second cover 2004 linearly along lateral axis 2302. First motor 2006 may include a pin 2006a, which is received by slot 2002s of first cover 2002. The rotation of pin 2006a may cause linear movement of first cover 2002. Second motor 2008 may include a pin 2008a, which is received by slot 2004s of second cover 2004, and which may work in a substantially similar manner as set forth above with respect to first motor 2006. First motor 2006 and second motor 2008 may be coupled to tray assembly frame 450 (referring to FIG. 16).

First motor 2006 and second motor 2008 each may include rotary encoders for controlling and monitoring the position of first cover 2002 and second cover 2004. First cover 2002 and second cover 2004 each may have home sensors (or limit switches) for indicating when first cover 2002 and second cover 2004 are in one or more designated positions, such as the positions shown in FIGS. 11-14. Such sensors for indicating these positions may include optical sensors (e.g., slotted optical sensors), proximity sensors, magnetic sensors, capacitive sensors, etc.

Figure 17:
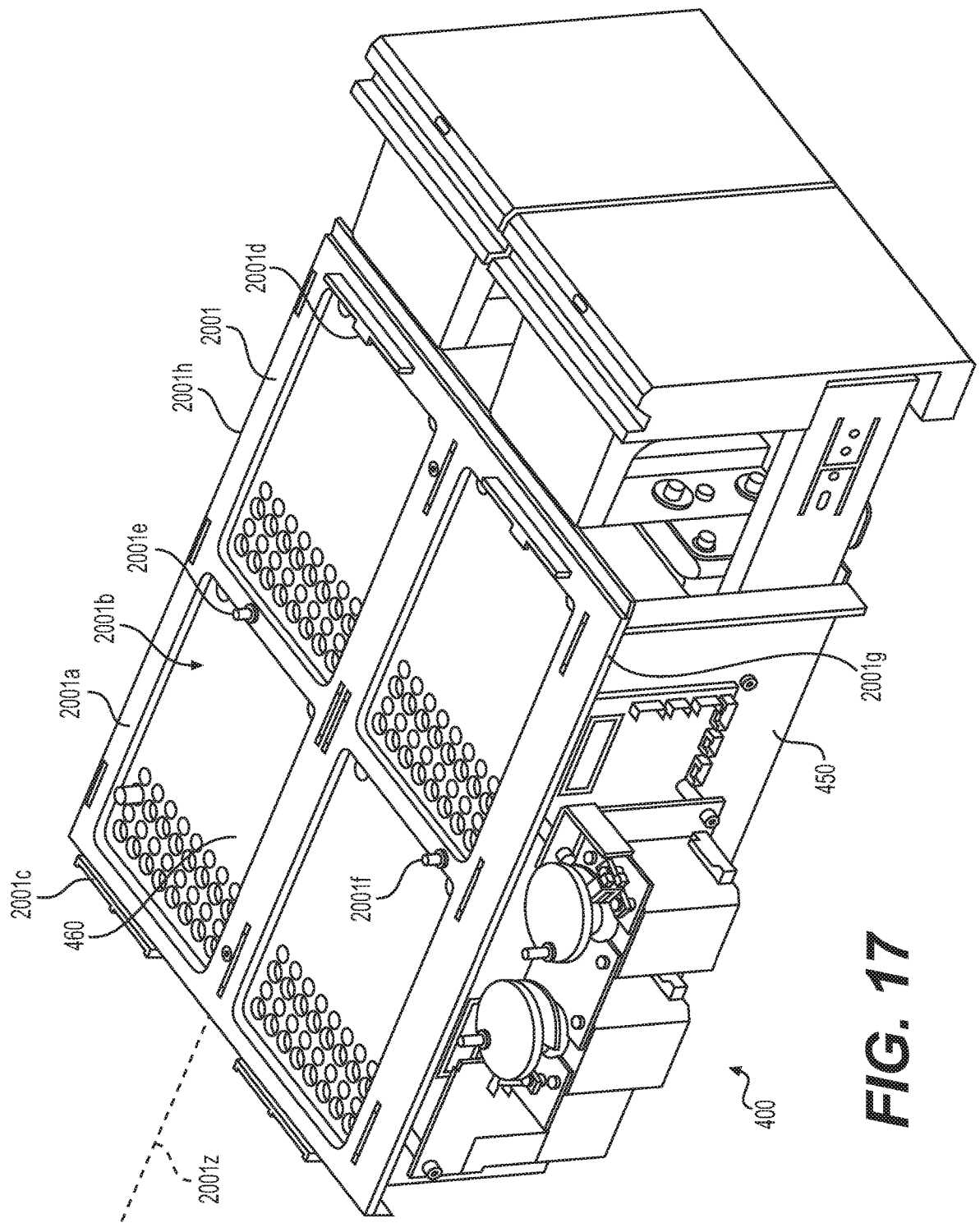
FIG. 17 is a perspective view of the tray assembly and the cover assembly of FIG. 16, with certain portions of the cover assembly removed.
Figure 18:
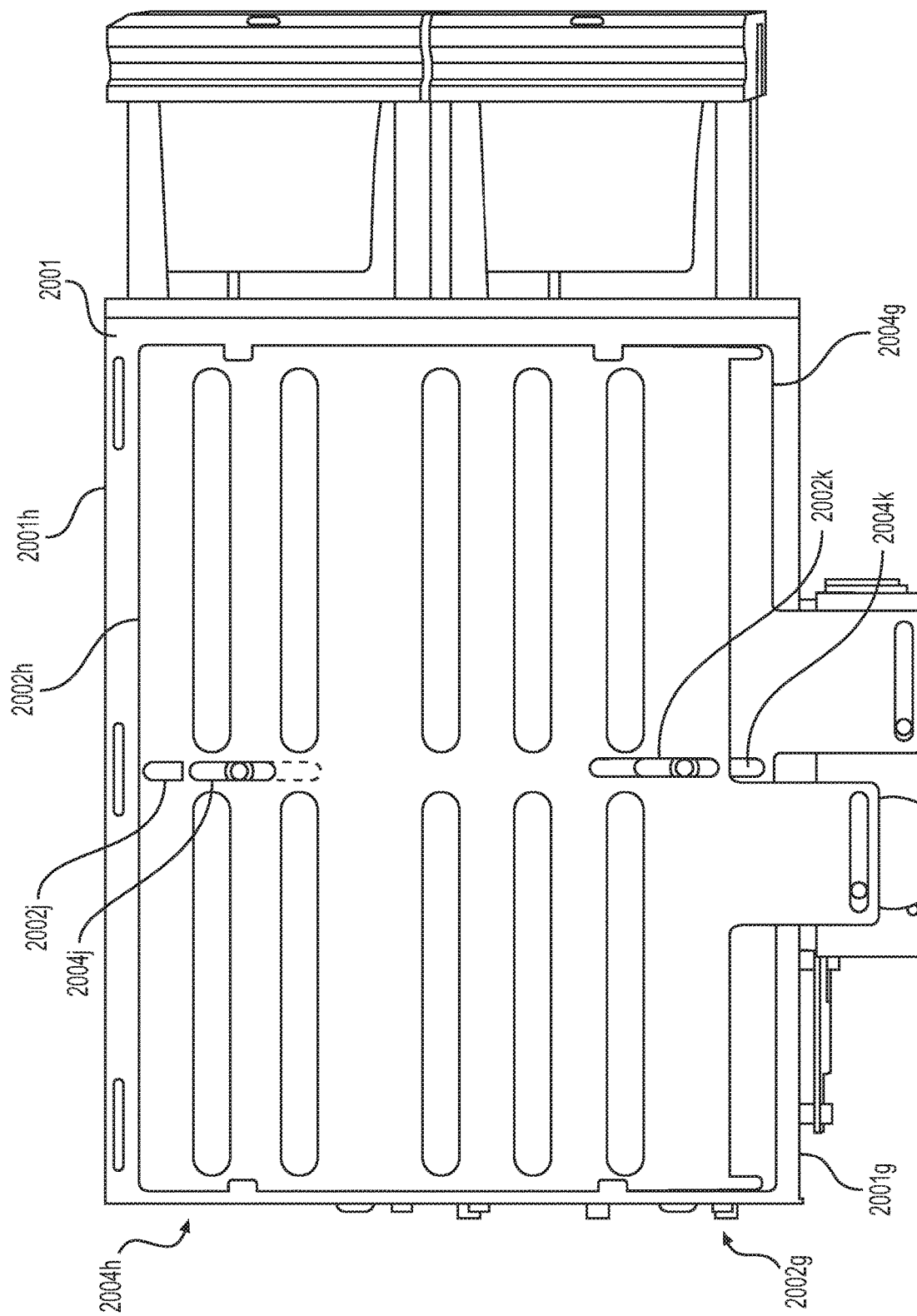
FIG. 18 is a top view of the tray assembly and the cover assembly shown in FIG. 16.

Referring to FIG. 17, cover frame 2001 may be mounted to a top surface of tray assembly frame 450, and may itself include a top surface 2001a. Cover frame 2001 also may include openings 2001b through which fluid transfer device 402 may access one or more receptacles. Openings 2001b may be arranged in the same manner in which trays 460 are arranged in second module 400. That is, when trays 460 are arranged in a two-by-two grid, openings 2001b also may be arranged in a two-by-two grid. Each opening 2001b may have dimensions suitable to enable fluid transfer device 402 to access wells positioned below cover frame 2001. For example, each opening 2001*b* may have length and width dimensions that are equal to or greater than the length and width of each tray 460. Alternatively, each opening 2001*b* may have a length and/or width that is less than the length and/or width of each tray 460, so long as each well contained by a tray 460 is still accessible through opening 2001*b*. However, if instead of a two-by-two grid, trays 460 were arranged in a three-by-three grid, openings 2001*b* may be arranged in a three-by-three grid.

Cover frame 2001 also may include one or more (e.g., at least two) guide rails 2001*c* that extend upward and away from top surface 2001*a*. Guide rails 2001*c* may be positioned along longitudinal edges of cover frame 2001, and may restrict and/or prevent the movement of first cover 2002 and second cover 2004 in the longitudinal direction. Guide rails 2001*c* also may include an inwardly extending tab 2001*d* that are configured to limit vertical movement of first cover 2002 and second cover 2004 (in a direction perpendicular the first and second planes of first cover 2002 and second cover 2004). Top surface 2001*a* and guide rail 2001*c* may serve as guides for the lateral movement of first cover 2002 and second cover 2004. In the examples shown, first cover 2002 is positioned beneath second cover 2004, such that first cover 2002 slides against top surface 2001*a*. Second cover 2004 may slide against tabs 2001*d*, and both first cover 2002 and second cover 2004 may slide against inwardly facing surfaces of guide rails 2001*c*. The interaction of first cover 2002 and second cover 2004 with top surface 2001*a* and guide rails 2001*c* (including tabs 2001*d*) help ensure that first cover 2002 and second cover 2004 move only in lateral directions (and not in longitudinal or in vertical up/down directions).

A guide pin 2001*e* and a guide pin 2001*f* each may extend upward and away from top surface 2001*a*. Guide pins 2001*e* and 2001*f* may be integral with cover frame 2001, or may extend through an aperture in cover frame 2001. Guide pins 2001*e* and 2001*f* may include a plastic bushing selected for low friction and high wear resistance. Guide pins 2001*e* and 2001*f* limit lateral movement of covers 2002 and 2004. For example, guide pin 2001*e* may be configured to limit movement of first cover 2002 and second cover 2004 laterally toward a lateral edge 2001*h*, and guide pin 2001*f* may be configured to limit movement of first cover 2002 and second cover 2004 laterally toward a lateral edge 2001*g*. Each of first slots 2002*j*, *k*, and second slots 2004*j*, *k*, may receive and/or otherwise accommodate one guide pin for limiting lateral movement of first cover 2002 and second cover 2004, respectively. Guide pin 2001*e* and guide pin 2001*f* may be spaced different distances from a longitudinal axis 2001*z* that is equidistant between laterally adjacent openings 2001*b* of cover frame 2001. In one embodiment, guide pin 2001*e* is positioned closer to longitudinal axis 2001*z* than guide pin 2001*f*. Because first slots 2002*j* and 2002*k* of first cover 2002 are spaced from lateral edges 2002*h* and 2002*g* by a same distance, the offset spacing of pins 2001*e* and 2001*f* enable pins 2001*e* and 2001*f* to engage lateral edges of first slots 2002*j* and 2002*k*, respectively, at different positions of first cover 2002. Thus, when first cover 2002 (or second cover 2004) is moved toward lateral edge 2001*h*, a lateral edge of first slot 2002*j* (or second slot 2004*j*) will contact guide pin 2001*e*, preventing further movement of first cover 2002 (or second cover 2004) toward lateral edge 2001*h*. While guide pin 2001*e* is engaged with the lateral edge of first slot 2002*j* (or second slot 2004*j*), guide pin 2001*f* may be spaced apart from each lateral edge of first slot 2002*k* (or second slot 2004*k*). When first cover 2002 (or second cover 2004) is moved toward lateral edge 2001*g*, a lateral edge of first slot 2002*k* (or second slot 2004*k*) will contact guide pin 2001*f*, preventing further movement of first cover 2002 (or second cover 2004) toward lateral edge 2001*g*. While guide pin 2001*f* is engaged with the lateral edge of first slot 2002*k* (or second slot 2004*k*), guide pin 2001*e* may be spaced apart from each lateral edge of first slot 2002*j* (or second slot 2004*j*).

In an alternative embodiment, a single motor may be coupled to both first cover 2002 and second cover 2004. For this implementation, cover assembly 2000 is open when the two covers are aligned, and closed when the two covers are out-of-phase with each other. In addition, the open arrangement must be positioned above the vial of interest (in this case, one of 3 positions). It is conceivable that one cover could be driven by a motor. The second cover would be able to slide independently. However, the second cover would be attached to springs that constantly push the free cover against a hard stop on the driven cover, thus aligning the two covers in the open position. A secondary hard stop would be located on the chassis frame such that if the motor-driven cover were moved to its full end-of-travel, the fixed hard stop would engage the free cover preventing the free cover from moving full travel and the springs would allow the free cover to remain fixed in position while the driven cover continues moving the final distance (thus creating the misaligned closed position.

Figure 11:
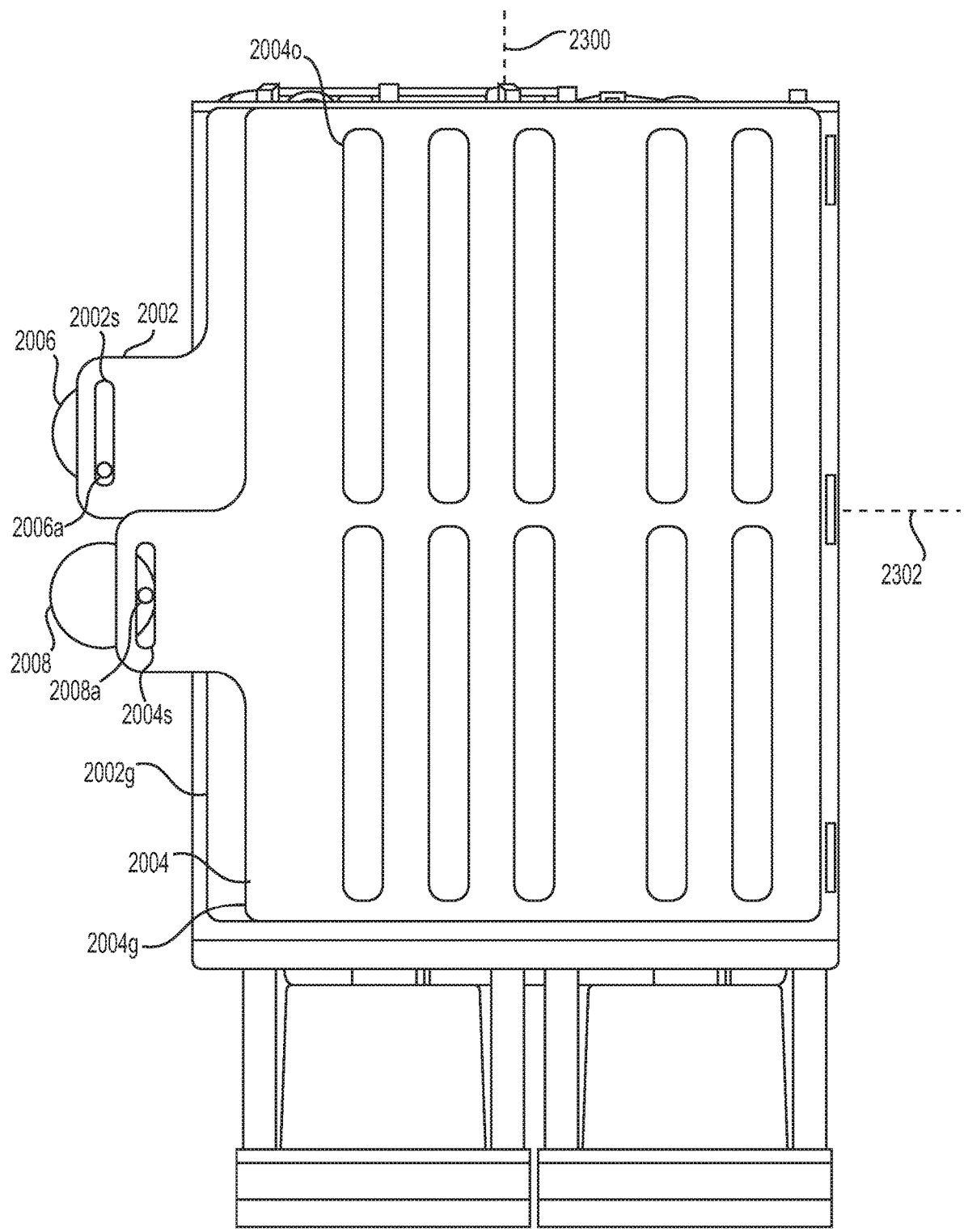
FIG. 11 is a top view of a cover assembly in a closed configuration.
Figure 12:
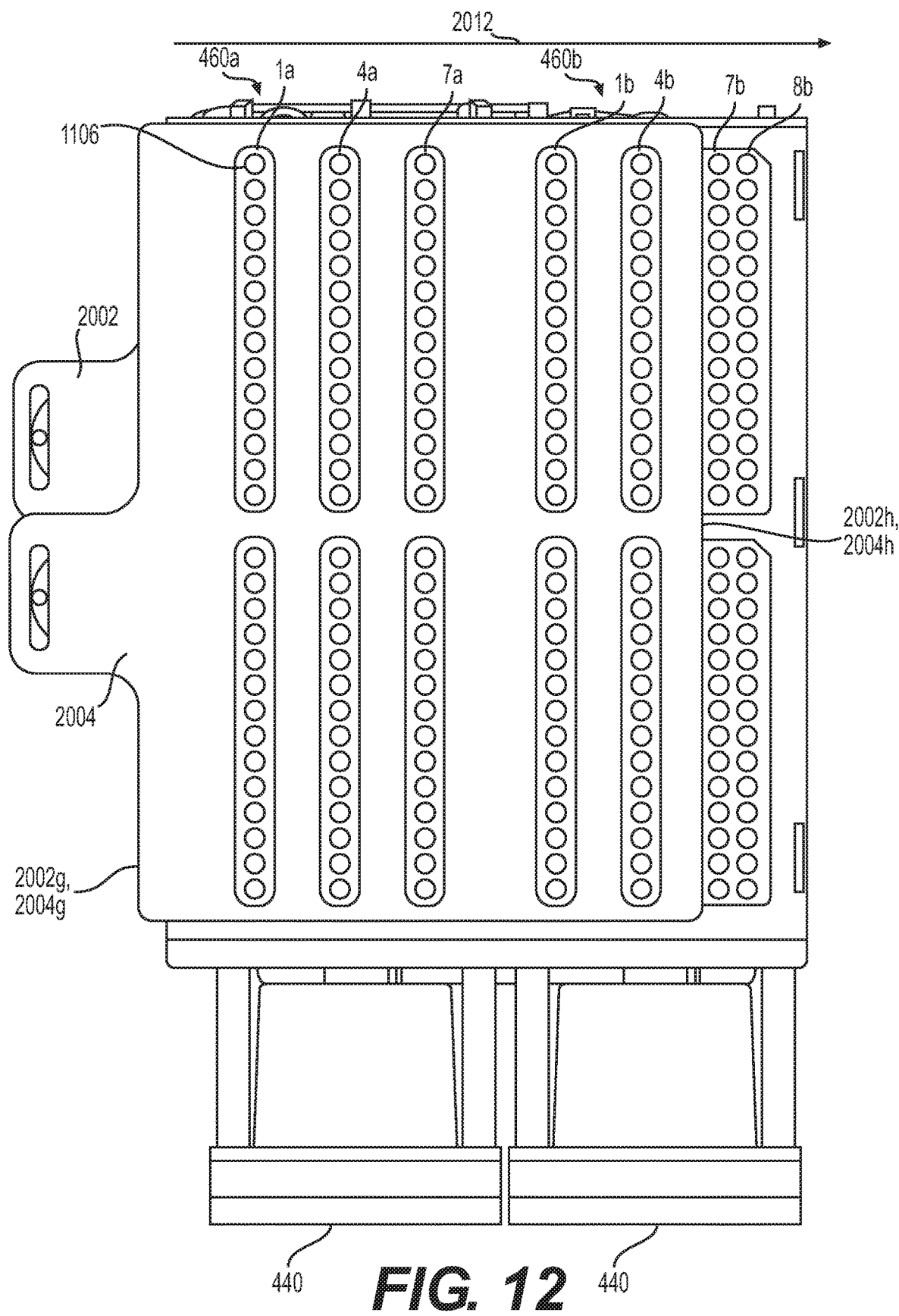
FIGS. 12-14 are top views of the cover assembly of FIG. 11 in different open configurations.
Figure 13:
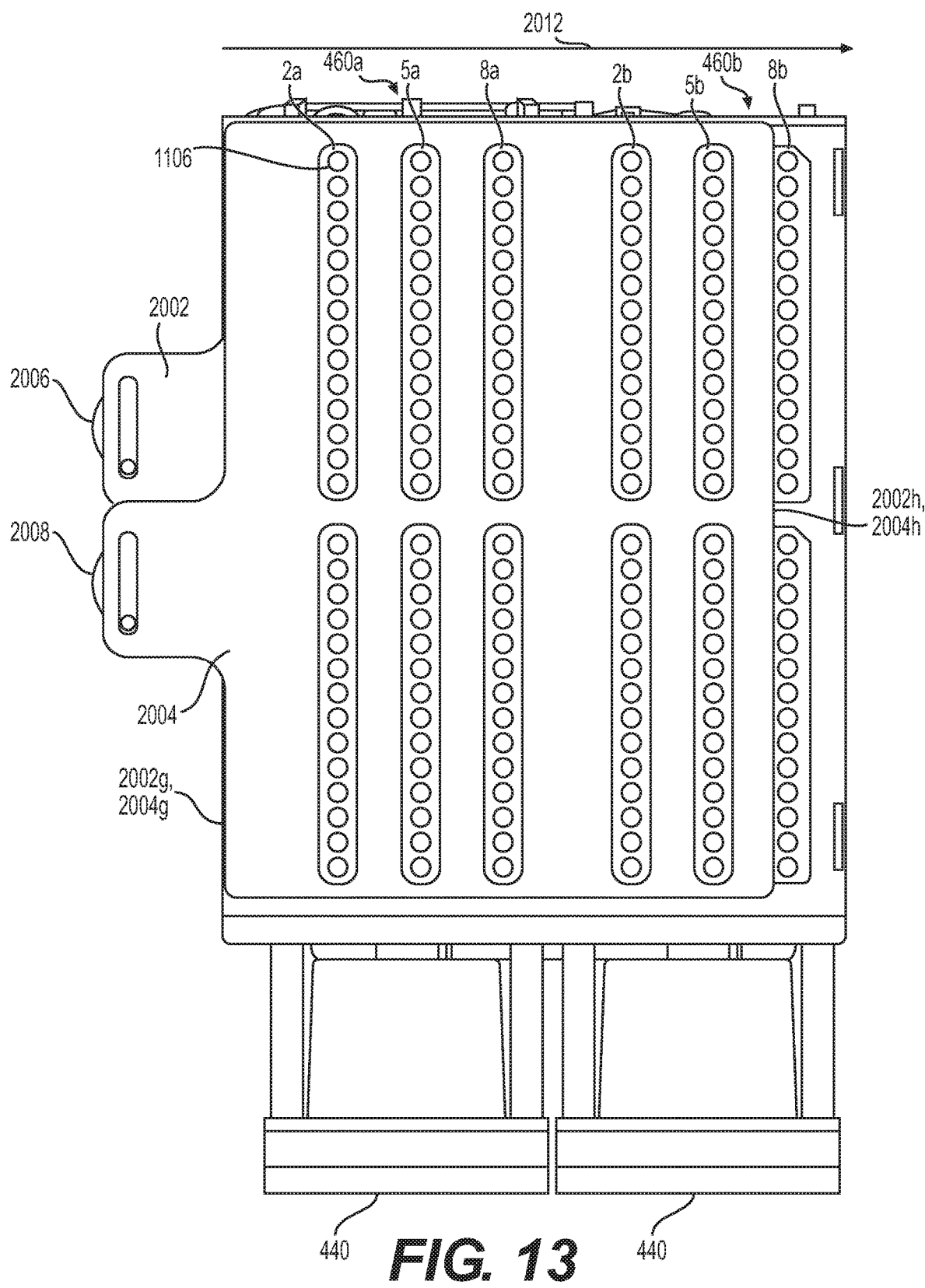
Figure 14:
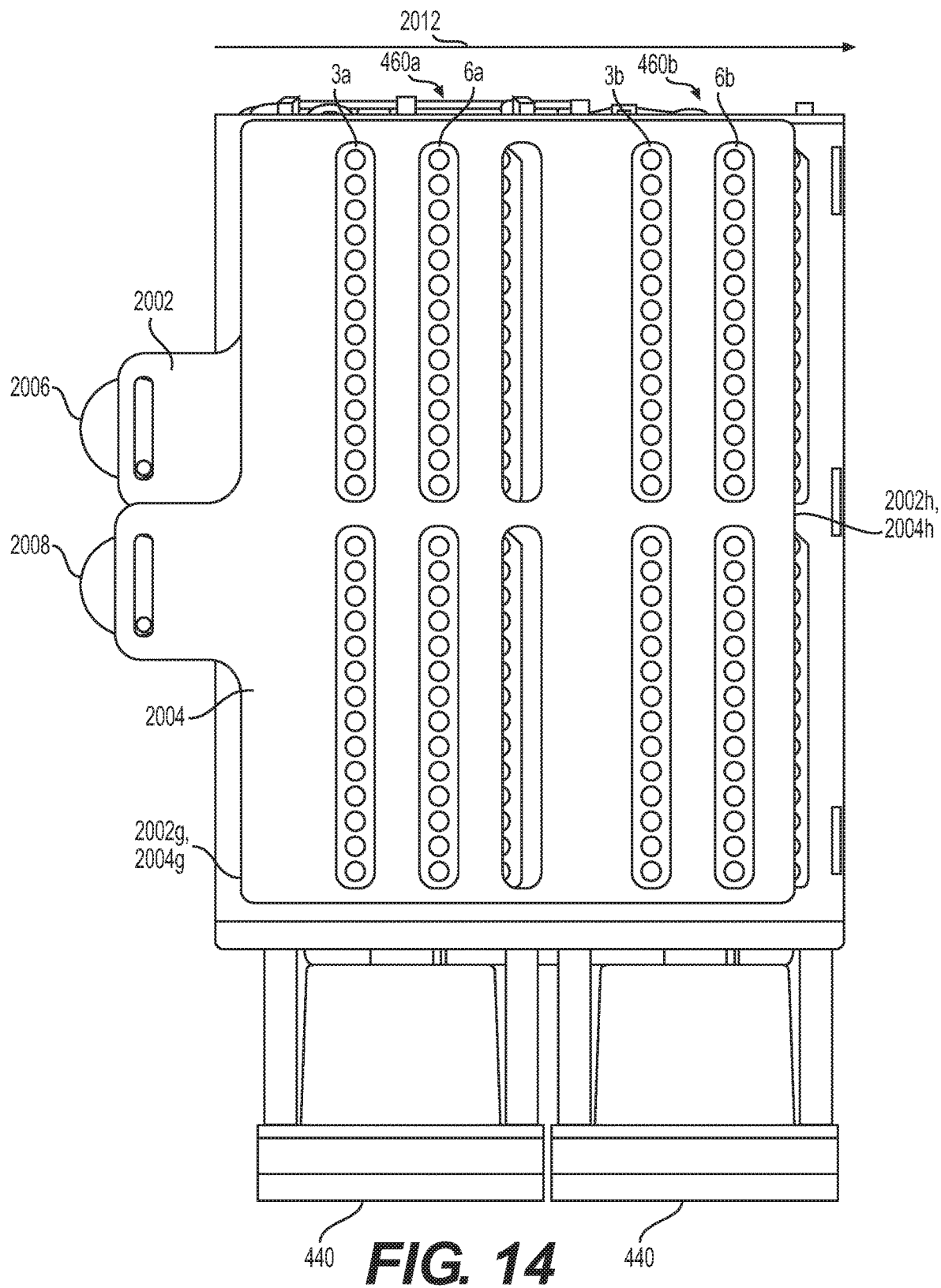

Cover assembly 2000 may be movable between one or more closed configurations (a fully closed configuration is shown in FIG. 11), and one or more open configurations, several examples of which are shown in FIGS. 12-14. In the fully closed configuration, at least one of first cover 2002 and second cover 2004 extends over each of the plurality of wells 1106 disposed underneath cover assembly 2000 to block or impede access to the plurality of wells. Thus, in the closed configuration, first cover 2002 and second cover 2004 may be laterally offset along lateral axis 2302 such that some openings of first cover 2002 are blocked by second cover 2004, and some openings of second cover 2004 are blocked by first cover 2002. In other words, in the closed configuration, tray holders 444 are inaccessible from any position directly above first cover 2002 and second cover 2004. When first cover 2002 and second cover 2004 are identically constructed, first lateral edges 2002*g* and 2004*g* may be distanced from one another along lateral axis 2302, and second lateral edges 2002*h* and 2004*h* may be distanced from one another along lateral axis 2302. In exemplary closed configuration arrangements, substance transfer pipettor 410 cannot access, and is unable to establish fluid communication with, any well 1106 when cover assembly 2000 is in the closed configuration. In other contemplated embodiments that do not feature a tray, the first cover 2002 and second cover 2004 are arranged to block or impede access by any fluid transfer device, or the like, to the microtiter well, receptacle, etc.

In various embodiments, to transition from the fully closed configuration to one or more of the open configurations, one or both of first cover 2002 and second cover 2004 may be moved laterally along lateral axis 2302 such that openings 2002*o* of first cover 2002 align with openings 2004*o* of second cover 2004, such that the aligned openings are situated over a column of wells 1106. In some of the open configurations, first lateral edges 2002*g* and 2004*g* may be aligned at the same position along lateral axis 2302, and second lateral edges 2002*h* and 2004*h* also may be aligned at the same position along lateral axis 2302. In the open configurations, a substantial entirety of first cover 2002 may be covered by second cover 2004, except for end tab 2002*i* of first cover 2002. That is, when viewed from a perspective above cover assembly 2000, end tab 2002*i* may be the only visible material of first cover 2002.

In various open configurations shown by FIGS. 12-14, a portion of at least one tray holder 444 and at least one of the plurality of wells 1106 are accessible through aligned openings of first cover 2002 and second cover 2004 by substance transfer pipettor 410. For example, as shown in FIGS. 12-14, each opening 2002*o* of first cover 2002 is aligned with an opening 2004*o* of second cover 2004. In the open configurations, a given pair of aligned openings 2002*o* and 2004*o* may be positioned over one or more wells, including, e.g., a column 1106*c* of wells 1106. Any well 1106 from the exposed column 1106*c* may be accessed through aligned openings 2002*o* and 2004*o*. In one example, a given pair of aligned openings 2002*o* and 2004*o* is positioned over only one column 1106*c*. However, in other examples, a given pair of aligned openings may be positioned over multiple columns of wells depending on the size and spacings of the openings and wells. As shown in each of FIGS. 12-14, multiple columns of a given tray 460 are accessible to substance transfer pipettor 410 while cover assembly 2000 is in a given open configuration. For example, as shown in FIG. 12, the first, fourth, and seventh columns of a tray 460*a* may be accessed in the first open configuration, while the first, fourth, seventh and eighth columns of a tray 460*b* may be accessed. The numbering of the columns of trays 460*a* and 460*b* is based on the orientation of the columns relative to a lateral vector 2012 (shown in FIGS. 12-14), with the first column of a given tray being encountered before the second column of a given tray along vector 2012, the second column being encountered before the third column, and so forth. Columns of tray 460*a* are marked 1*a*-8*a*, and columns of tray 460*b* are marked 1*b*-8*b*, in FIGS. 12-14.

In the second open configuration shown in FIG. 13, the second, fifth, and eighth columns of tray 460*a* may be accessed, while the second, fifth, and eighth columns of tray 460*b* may be accessed. In the third open configuration shown in FIG. 14, the third and sixth columns of both trays 460*a* and 460*b* may be accessed.

To move from the first open configuration shown in FIG. 12 to the second open configuration shown in FIG. 13, at least one of first cover 2002 and second cover 2004 may be moved along lateral axis 2302. In one example, both first cover 2002 and second cover 2004 may be moved by a same distance in a same direction along lateral axis 2302. This lateral movement of both first cover 2002 and second cover 2004 allows for different columns of wells 1106 to be accessible to substance transfer pipettor 410 than are accessible to substance transfer pipettor 410 in the first open configuration. To move from the first open configuration to the second open configuration, first cover 2002 and second cover 2004 may be moved along lateral axis 2302 by a distance that is substantially equal to a distance between the centers of adjacent columns of wells 1106. To move from the second open configuration to the third open configuration shown in FIG. 14, first cover 2002 and second cover 2004 may be moved along lateral axis 2302 in the same direction by the same distance as previously discussed.

First cover 2002 and second cover 2004 also may include additional closed configurations other than the fully closed configuration shown in FIG. 11. For example, instead of reverting to the closed configuration of FIG. 11 after each open configuration, first cover 2002 and second cover 2004 may be moved relative to one another to achieve different, intermediate closed configurations. For example, to move from any of the open configurations shown in FIGS. 12-14 to an intermediate closed configuration, first cover 2002 may be kept stationary while second cover 2004 is moved linearly along lateral axis 2302 by a distance, or second cover 2004 may be kept stationary while first cover 2002 is moved linearly along lateral axis 2302 by the same distance. Keeping one of the first cover 2002 and second cover 2004 stationary allows each opening of first cover 2002 and second cover 2004 to be blocked without having to move both first cover 2002 and second cover 2004 to the positions shown in FIG. 11. This may result in reduced procedural times because, depending on the anticipated path of substance transfer pipettor 410, first cover 2002 and second cover 2004 may be moved over a shorter distance while still covering wells 1106 underneath the travelling path of substance transfer pipettor 410. The material of first cover 2002 and second cover 2004 that surround the openings of the covers may constitute a "flight path" of substance transfer pipettor 410 in some embodiments. That is, a path over which substance transfer pipettor 410 moves to limit contamination (e.g., droplets falling into the wrong vials).

Method of Use

Figure 15:
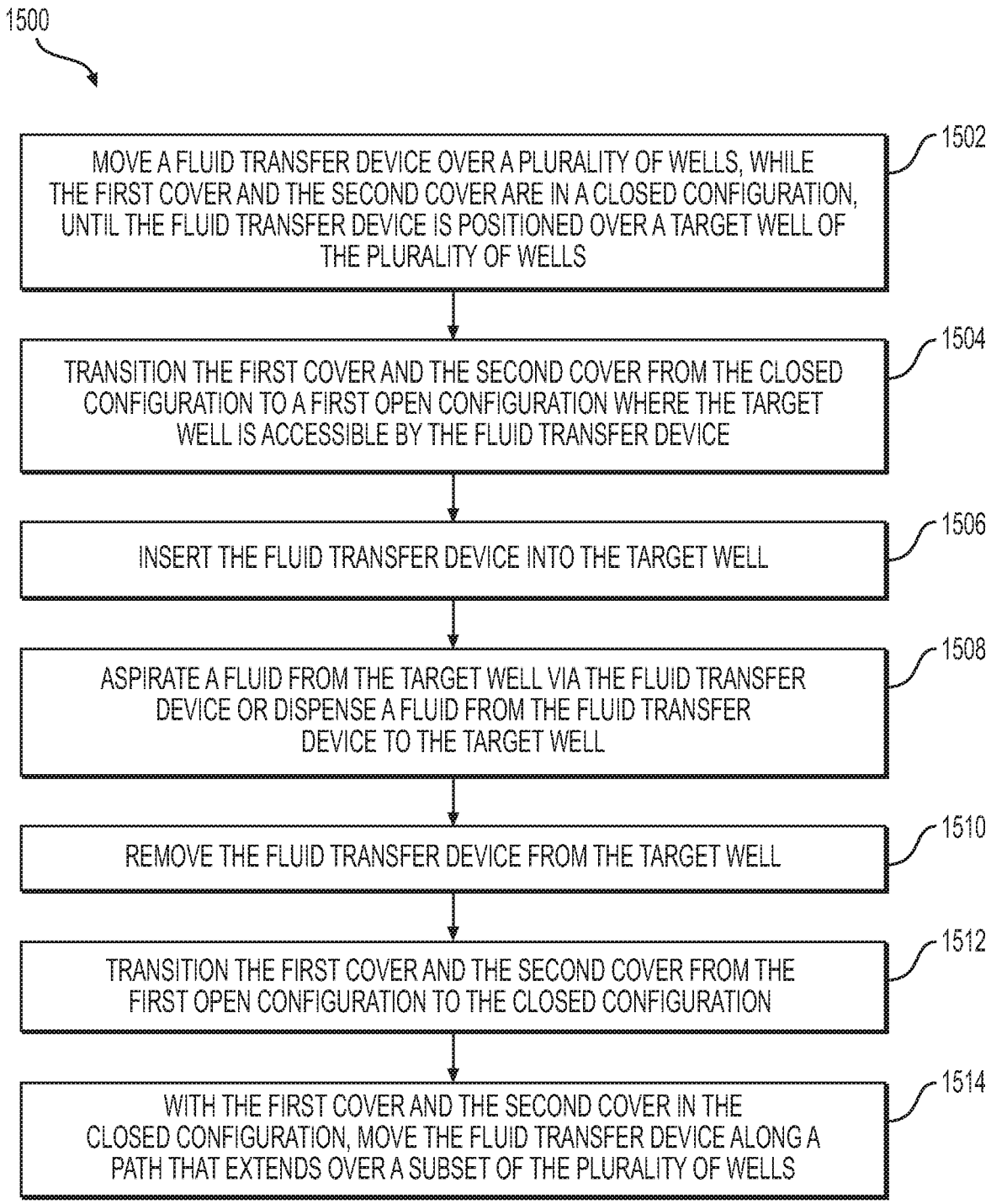
FIG. 15 is a flowchart of a method of aspirating or dispensing fluid according to the disclosure.

A method 1500 is shown in FIG. 15. Method 1500 may start at step 1502, where, while first cover 2002 and second cover 2004 are in a closed configuration, substance transfer pipettor 410 may be moved over one or more wells 1106, until substance transfer pipettor 410 is positioned over a target well 1106 of the one or more wells 1106. Because first cover 2002 and second cover 2004 are in a closed configuration, any fluids and/or other any substances that drip from substance transfer pipettor 410 may be caught by first cover 2002 and/or second cover 2004, instead of dripping into wells 1106.

Method 1500 then may proceed to step 1504, where, first cover 2002 and second cover 2004 may be transitioned from a closed configuration to a first open configuration (e.g., one of the configurations shown in FIGS. 12-14), where the target well is accessible to substance transfer pipettor 410. In the first open configuration, an opening 2002*o* of first cover 2002 may be aligned with an opening 2004*o* of second cover 2004 to provide access to the target well through the aligned openings. In certain open configurations of first cover 2002 and second cover 2004, each receptacle of a given row of receptacles underneath first cover 2002 and second cover 2004 may be accessible to substance transfer pipettor 140. Method 1500 then may proceed to step 1506, where substance transfer pipettor 410 is inserted into the target well through the pair of aligned openings 2002*o* and 2004*o*. Then, method 1500 may proceed to step 1508, where a liquid may be aspirated from the target well via substance transfer pipettor 410, or a liquid may be dispensed from substance transfer pipettor 410 into the target well. For example, one or more of reagent, oil, and/or sample mixture may be dispensed by fluid transfer device 402 into a vial 464 positioned in the target well. For example, the reagent may be reconstituted reagent from a mixing well of a PCR reagent pack. The reagent may provide the ingredients necessary for performing PCR in a premixed and optimized format, such as, e.g., Taq DNA polymerase, deoxynucleoside triphosphates (dNTPs), and magnesium chloride (MgCl2). The sample mixture may include nucleic acid material to be amplified.

Once liquid has been dispensed or aspirated at step 1508, method 1500 may proceed to step 1510, where substance transfer pipettor 410 is removed from the target well, and to step 1512, where, first cover 2002 and second cover 2004 are moved from the first open configuration to a closed configuration, such as, e.g., the fully closed configuration shown in FIG. 11, or one of the additional closed configurations described above. At step 1514, with first cover 2002 and second cover 2004 in a closed configuration, substance transfer pipettor 410 may be moved along a path that extends over at least a subset of wells other than the target well. Thus, in some examples, substance transfer pipettor 410 may not travel over any wells 1106 unless one or both of first cover 2002 and second cover 2004 is disposed between substance transfer pipettor 410 and the wells 1106.

The steps depicted in FIG. 15 are not intended to limit the embodiments described herein to sequential steps. For example, some of the steps of method 1500 may occur simultaneously or overlap in time to some extent, if, for example, additional throughput is desired. For example, substance transfer pipettor 410 may be moved while one or both of first cover 2002 and/or second cover 2004 are moved. While this overlapping of steps may increase a chance of contamination by inadvertent dripping of sample or reagent into an exposed well 1106, such an overlapping of steps may produce a benefit of improved workflow times and processes that is desirable in certain embodiments. Moreover, in some embodiments, the location of the target well in relation to the travel path of the substance transfer pipettor 410 may allow for the overlapping of one or more steps without subjecting any open wells 1106 to the risk of contamination. It can be appreciated then that an improved workflow may be achieved by the overlapping of steps, at various coordinated times, without the risk, or increased risk, of contamination.

In various embodiments, the movement of substance transfer pipettor 410 at steps 1502 and 1514 can be simultaneous along multiple axes. That is, substance transfer pipettor 410 may move simultaneously in X and Y directions (and in some cases, also in the Z direction). The ability to move simultaneously along multiple axes may allow substance transfer pipettor 410 to take shorter and more direct paths between different locations during a procedure, reducing overall procedure time. Because of the presence of cover assembly 2000, the path of substance transfer pipettor 410 may travel directly over one or more wells 1106 positioned below substance transfer pipettor 410, increasing path efficiency while reducing the risk of contaminating wells below the path of substance transfer pipettor 410. Additionally, the reduced procedure time may increase throughput of diagnostic system 10.

Likewise, intermediate closed configurations may be used in order to optimize procedure timing. For example, instead of returning to the fully closed configuration shown in FIG. 12 after transitioning to each open configuration, which would require both first cover 2002 and second cover 2004 to move back to the positions shown in FIG. 11 (regardless of where they were presently located), one of first cover 2002 and second cover 2004 can be kept stationary, while the other of first cover 2002 and second cover 2004 is moved. These alternative closed configurations may not cover each well underneath cover assembly 2000, but could cover all wells underneath an anticipated path of substance transfer pipettor 410. In other instances, an alternative closed configuration may cover all wells directly underneath an anticipated path, and additionally a subset of surrounding wells that may be at risk of contamination due to splashing of liquid. In some examples, therefore, the closed configuration selected during operation may depend on the path of substance transfer pipettor 410.

In some examples, a controller may coordinate a travel path of substance transfer pipettor 410, and the movement of cover assembly 2000 between open and closed configurations based on input from positioning sensors coupled to both substance transfer pipettor 410 and cover assembly 2000. The controller may receive instructions regarding a procedure to be performed. Based on the received instructions, which may include a various locations for substance transfer pipettor 410 to travel to during the procedure, the controller may determine, in real-time, an optimal travel path of substance transfer pipettor 410 and an optimal sequence for opening and closing cover assembly 2000. The optimal travel path and optimal sequence may be determined based on, e.g., the current and anticipated positions of substance transfer pipettor 410 and cover assembly 2000. In some examples, the travel path of substance transfer pipettor 410 and the sequence for opening and closing cover assembly 2000 may be preset for certain procedures.

Each of the U.S. Patent Applications, U.S. Patent Application Publications and U.S. Patents referred to in the specification is incorporated herein by reference in its entirety.

It will be apparent to those skilled in the art that various modifications and variations may be made in the disclosed systems and processes without departing from the scope of the disclosure. Other examples of the disclosure will be apparent to those skilled in the art from consideration of the specification and practice of the disclosure disclosed herein. It is intended that the specification and examples be considered as exemplary only.

We claim:

1. A cover assembly, comprising:
 a tray assembly frame;
 a first cover supported by the tray assembly frame, the first cover extending in a first plane and defining one or more first holes, each of the one or more first holes having an enclosed boundary defined by material of the first cover;
 a second cover supported by the tray assembly frame, the second cover extending in a second plane and defining one or more second holes, each of the one or more second holes having an enclosed boundary defined by material of the second cover, wherein the first and second planes are different planes, and wherein the second cover is disposed above the first cover;
 one or more tray holders, each of the one or more tray holders being configured to hold at least one tray in an upright orientation, each of the one or more tray holders being moveable between an open position and a closed position, each of the one or more tray holders being accessible for loading or removing the at least one tray in the open position, and the one or more tray holders being positioned beneath the first and second covers in the closed position;
 one or more drawers, each of the one or more tray holders being coupled to one of the one or more drawers, and each drawer being coupled to a drawer face for moving the one or more tray holders between the open and closed positions; and
 a first actuator and a second actuator coupled to the tray assembly frame and to the first and second covers, the first actuator and the second actuator being configured to laterally move the first and second covers in the first and second planes, respectively, between a closed configuration and one or more open configurations, such that the first and second covers are substantially parallel to each other in the closed configuration and the one or more open configurations, wherein the one or more tray holders are inaccessible from any position directly above the first and second covers in the closed configuration, and wherein at least one of the one or more first holes and at least one of the one or more second holes are aligned and configured to permit access by a fluid transfer device, through both the at least one of the one or more first holes and the at least one of the one or more second holes, to a portion of at least one of the one or more tray holders in the one or more open configurations.

2. The cover assembly of claim 1, further comprising a cover frame coupled to at least a portion of a top surface of the tray assembly frame and dimensioned to permit access to the one or more tray holders, the cover frame including at least two opposed, upwardly extending guide rails, the at least two opposed upwardly extending guide rails being configured to limit longitudinal movement of the first and second covers, wherein each guide rail includes an inwardly extending tab configured to limit vertical movement of the first and second covers.

3. The cover assembly of claim 2, further comprising one or more guide pins extending upwardly from or through the cover frame, the first cover defining one or more laterally extending, first guide slots that accommodate the one or more guide pins, the second cover defining one or more laterally extending second guide slots that accommodate the one or more guide pins, wherein each of the one or more first guide slots and the one or more second guide slots is associated with one of the one or more guide pins, wherein the one or more first guide slots and the one or more second guide slots are coextensive with each other, and wherein the one or more guide pins and the one or more first guide slots and the one or more second guide slots are dimensioned to limit lateral movement of the first and second covers.

4. The cover assembly of claim 1, wherein the first and second covers contact each other and are configured for sliding engagement.

5. The cover assembly of claim 1, wherein the first cover defines a plurality of first holes.

6. The cover assembly of claim 5, wherein the second cover defines a plurality of second holes.

7. The cover assembly of claim 6, wherein, in each of the one or more open configurations, each of the one or more first holes is aligned with a corresponding one of the one or more second holes, and wherein each of the aligned first and second holes permits access by the fluid transfer device to a portion of at least one of the one or more tray holders in the one or more open configurations.

8. The cover assembly of claim 6, wherein for each of the one or more first holes there is a corresponding one of the one or more second holes.

9. The cover assembly of claim 1, wherein the first and second covers have substantially the same dimensions, and wherein the locations and dimensions of the one or more first holes defined by the first cover and the one or more second holes defined by the second cover are substantially the same.

10. The cover assembly of claim 9, wherein the first cover and the second cover are arranged in a reversed orientation about a lateral axis along which the first cover or the second cover moves.

11. The cover assembly of claim 1, wherein the first plane is defined by a first longitudinal axis and a first lateral axis that is perpendicular to the first longitudinal axis, the first cover being configured to move in the first plane along the first lateral axis and not along the first longitudinal axis, and wherein the second plane is defined by a second longitudinal axis and a second lateral axis that is perpendicular to the second longitudinal axis, the second cover being configured to move in the second plane along the second lateral axis and not along the second longitudinal axis.

12. The cover assembly of claim 1, wherein the first actuator and the second actuator are configured to move the first and second covers independent of each other.

13. The cover assembly of claim 12, wherein the first actuator includes a first motor coupled to the first cover and the second actuator includes a second motor coupled to the second cover.

14. The cover assembly of claim 13, wherein the first cover comprises a first edge that defines a first end tab and a first lateral edge opposite the first edge, and wherein the second cover comprises a second edge that defines a second end tab and a second lateral edge opposite the second edge.

15. The cover assembly of claim 14, wherein the first end tab defines a first slot, the first actuator includes a first pin, the first slot receives the first pin, and rotation of the first pin causes linear movement of the first cover, and wherein the second end tab defines a second slot, the second actuator includes a second pin, the second slot receives the second pin, and rotation of the second pin causes linear movement of the second cover.

16. The cover assembly of claim 1, wherein the one or more first holes and the one or more second holes are linear holes.

17. The cover assembly of claim 16, wherein the width of each linear hole is from about 5 mm to about 15 mm.

18. The cover assembly of claim 16, wherein the width of each linear hole is at least about 10 mm.

19. The cover assembly of claim 17, wherein the length of each linear hole is from about 5 to about 15 times the width of the linear hole.

20. The cover assembly of claim 19, wherein the length of each linear hole is about 10 times the width of the linear hole.

21. The cover assembly of claim 1, wherein the one or more actuators are configured to slide the first cover in the first plane and slide the second cover in the second plane.

22. A method of aspirating or dispensing a fluid with a system having a first cover coupled to a first actuator, a second cover coupled to s second actuator, and a fluid transfer device, wherein the first cover and the second cover are disposed above a plurality of receptacles; the method comprising the steps of:
(a) laterally transitioning the first cover and/or the second cover from a first closed configuration; where access to a first group of the plurality of receptacles by the fluid transfer device is blocked by the first cover and/or the second cover, to a first open configuration, where a first receptacle of the first group of receptacles is accessible by the fluid transfer device through both a first hole of the first cover and a second hole of the second cover, such that the first and second covers are substantially parallel to each other in the first open configuration, the first hole having an enclosed boundary defined by material of the first cover and the second hole having an enclosed boundary defined by material of the second cover;
(b) aspirating the fluid from the first receptacle of the first group of receptacles using the fluid transfer device or dispensing the fluid into the first receptacle using the fluid transfer device; and
(c) after step (b), laterally transitioning the first cover and/or the second cover from the first open configuration to the first closed configuration in a first plane and a second plane, respectively, or to a second closed configuration, where access to a second group of the plurality of receptacles by the fluid transfer device positioned above the first cover and the second cover is blocked by the first cover and/or the second cover, such that the first and second covers are substantially parallel to each other in at least the first closed configuration.

23. The method of claim 22, wherein the first cover and the second cover move independent of each other during the transitioning steps.

24. The method of claim 22, further comprising a step of lowering the fluid transfer device through the first hole of the first cover and the second hole of the second cover prior to step (b).

25. The method of claim 24, wherein the first cover is disposed in the first plane, and the first hole is aligned with the second hole in the first open configuration, thereby permitting the fluid transfer device to access the first receptacle of the first group of receptacles.

26. The method of claim 22, further comprising, prior to step (a) or after step (c), a step of moving the fluid transfer device along a path that extends over at least one receptacle of the plurality of receptacles, the path being covered by the first cover and/or the second cover.

27. The method of claim 26, further comprising, after step (c), a step of transitioning the first and second covers to a second open configuration where a second receptacle of the second group of receptacles is accessible by the fluid transfer device and access to the first receptacle of the first group of receptacles by the fluid transfer device is blocked by the first cover and/or the second cover.

28. The method of claim 27, further comprising, after the step of transitioning the first and second covers to the second open configuration, a step of aspirating the fluid from the second receptacle of the second group of receptacles using the fluid transfer device or dispensing the fluid into the second receptacle of the second group of receptacles using the fluid transfer device.

29. The method of claim 22, wherein the first cover or the second cover is stationary when transitioning the first and second covers from the first closed configuration to the first open configuration.

30. The method of claim 22, wherein the first and second covers move simultaneously when transitioning the first and second covers from the first closed configuration to the first open configuration.

31. The method of claim 22, wherein the first and second covers move sequentially when transitioning the first and second covers from the first closed configuration to the first open configuration.

32. The method of claim 22, further comprising, prior to step (a), a step of providing one or more trays to the system below the first and second covers, each of the one or more trays supporting or comprising at least a portion of the plurality of receptacles.

33. The method of claim 32, wherein each of the one or more trays comprises a plurality of wells, each of the plurality of wells being configured to hold one of the plurality of receptacles or a cap for closing an associated one of the plurality of receptacles, and each of the plurality of receptacles being a vial.

34. The method of claim 33, further comprising, with the fluid transfer device, a step of engaging a cap supported by a first well of the plurality wells in a frictional fit and a step of sealing a vial in a second well of the plurality of wells with the cap, thereby forming a cap/vial assembly, wherein the first and second weds are adjacent wells.

35. The method of claim 34, further comprising, while the cap of the cap/vial assembly is engaged by the fluid transfer device, a step of moving the cap/vial assembly from a first location of the system, where the engaging and sealing steps are performed, to a second location of the system.

36. The method of claim 35, wherein the second location of the system is a centrifuge or a thermal cycler.

37. The method of claim 22, wherein step (b) comprises dispensing the fluid into the first receptacle, and wherein the fluid is a reaction fluid for performing a RCA reaction.

38. The method of claim 22, further comprising, prior to step (b), a step of inserting a fixed or disposable tip of the quid transfer device into the first receptacle.

39. A method of aspirating or dispensing a fluid with a system having a first cover coupled to a first actuator, a second cover coupled to a second actuator, and a fluid transfer device, wherein the first cover and the second cover are disposed above a plurality of receptacles, the method comprising the steps of:
 (a) laterally transitioning the first cover and/or the second cover from a first closed configuration, where access to at least a first row of the plurality of receptacles by the fluid transfer device is blocked by the first cover and/or the second cover, to a first open configuration, where the first row of receptacles is accessible by the fluid transfer device, through both a first hole of the first cover and a second hole of the second cover, such that the first and second covers are substantially parallel to each other in the first open configuration, the first hole having an enclosed boundary defined by material of the first cover and the second hole having an enclosed boundary defined by material of the second cover;
 (b) aspirating the fluid from the first receptacle using the fluid transfer device or dispensing the fluid into the first receptacle using the fluid transfer device; and
 (c) after step (b), laterally transitioning the first cover and the second cover from the first open configuration to the first closed configuration in a first plane and a second plane, respectively, or to a second closed configuration, where access to at least a second row of the plurality of receptacles by the fluid transfer device positioned above the first cover and the second cover is blocked by the first cover and/or the second cover, such that the first and second covers are substantially parallel to each other in at least the first closed configuration.

* * * * *

UNITED STATES PATENT AND TRADEMARK OFFICE
CERTIFICATE OF CORRECTION

PATENT NO. : 11,285,486 B2
APPLICATION NO. : 15/934758
DATED : March 29, 2022
INVENTOR(S) : David Buse It is certified that error appears in the above-identified patent and that said Letters Patent is hereby corrected as shown below:

In the Claims

Column 20, Line 38, in Claim 21, "slide" should read as --to slide--.
Column 20, Line 41, in Claim 22, delete "s second" and insert --a second--.
Column 20, Line 43, in Claim 22, delete "receptacles;" and insert --receptacles,--.
Column 20, Line 46, in Claim 22, delete "configuration;" and insert --configuration,--.
Column 22, Line 6, in Claim 34, delete "plurality wells" and insert --plurality of wells--.
Column 22, Line 9, in Claim 34, delete "weds" and insert --wells--.
Column 22, Line 19, in Claim 37, delete "RCA" and insert --PCR--.
Column 22, Line 22, in Claim 38, delete "quid" and insert --fluid--.

Signed and Sealed this
Nineteenth Day of July, 2022

Katherine Kelly Vidal
*Director of the United States Patent and Trademark Office*